(12) United States Patent
Walt et al.

(10) Patent No.: US 11,237,171 B2
(45) Date of Patent: Feb. 1, 2022

(54) METHODS AND ARRAYS FOR TARGET ANALYTE DETECTION AND DETERMINATION OF TARGET ANALYTE CONCENTRATION IN SOLUTION

(71) Applicant: Trustees of Tufts College, Medford, MA (US)

(72) Inventors: David R. Walt, Boston, MA (US); David M. Rissin, Somerville, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 7 days.

(21) Appl. No.: 16/286,811

(22) Filed: Feb. 27, 2019

(65) Prior Publication Data
US 2019/0293655 A1 Sep. 26, 2019

Related U.S. Application Data

(63) Continuation of application No. 15/205,497, filed on Jul. 8, 2016, now Pat. No. 10,261,089, which is a continuation of application No. 14/638,254, filed on Mar. 4, 2015, now Pat. No. 9,395,359, which is a continuation of application No. 13/870,596, filed on Apr. 25, 2013, now abandoned, which is a continuation of application No. 11/707,385, filed on
(Continued)

(51) Int. Cl.
*G01N 33/58* (2006.01)
*C12Q 1/6837* (2018.01)
*G01N 33/543* (2006.01)

(52) U.S. Cl.
CPC ......... *G01N 33/581* (2013.01); *C12Q 1/6837* (2013.01); *G01N 33/543* (2013.01); *G01N 33/54346* (2013.01); *G01N 33/54366* (2013.01); *G01N 33/54386* (2013.01); *G01N 2333/938* (2013.01)

(58) Field of Classification Search
CPC .......... G01N 33/54366; G01N 33/581; G01N 33/543; G01N 2333/938; G01N 33/54386; G01N 33/54346; C12Q 1/6837; C12Q 2527/143
See application file for complete search history.

(56) References Cited

U.S. PATENT DOCUMENTS 3,712,986 A  1/1973 Collings
4,200,110 A  4/1980 Peterson et al.
(Continued)

FOREIGN PATENT DOCUMENTS

AU  199956253 B2  3/2000
CN  1635146 A  7/2005
(Continued)

OTHER PUBLICATIONS

Rondelez et al. (Nature Biotechnology Letters. 2005. vol. 23(3):361-365). (Year: 2005).*
(Continued)

*Primary Examiner* — Jana A Hines
(74) *Attorney, Agent, or Firm* — Hayes Soloway PC

(57) ABSTRACT

Arrays of single molecules and methods of producing an array of single molecules are described. Arrays with defined volumes between 10 attoliters and 50 picoliters enable single molecule detection and quantitation.

19 Claims, 8 Drawing Sheets

Related U.S. Application Data

Feb. 16, 2007, now Pat. No. 8,460,879, application No. 13/870,596, which is a continuation of application No. 11/707,383, filed on Feb. 16, 2007, now Pat. No. 8,460,878, application No. 13/870,596, which is a continuation of application No. 11/707,384, filed on Feb. 16, 2007, now Pat. No. 8,492,098.

(60) Provisional application No. 60/792,736, filed on Apr. 17, 2006, provisional application No. 60/775,692, filed on Feb. 21, 2006.

(56) References Cited

U.S. PATENT DOCUMENTS

| | | |
|---|---|---|
| 4,232,119 A | 11/1980 | Carlsson et al. |
| 4,631,211 A | 12/1986 | Houghten |
| 4,780,421 A | 10/1988 | Kameda et al. |
| 4,883,642 A | 11/1989 | Bisconte |
| 4,907,037 A | 3/1990 | Boisde et al. |
| 4,924,870 A | 5/1990 | Wlodarczyk et al. |
| 4,962,037 A | 10/1990 | Jett et al. |
| 5,026,159 A | 6/1991 | Allen et al. |
| 5,028,535 A | 7/1991 | Buechler et al. |
| 5,089,391 A | 2/1992 | Buechler et al. |
| 5,091,300 A | 2/1992 | Hurni et al. |
| 5,108,961 A | 4/1992 | Zhong et al. |
| 5,152,816 A | 10/1992 | Berkey |
| 5,190,857 A | 3/1993 | Allen et al. |
| 5,196,306 A | 3/1993 | Bobrow et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,315,375 A | 5/1994 | Allen |
| 5,320,814 A | 6/1994 | Walt et al. |
| 5,329,461 A | 7/1994 | Allen et al. |
| 5,374,395 A | 12/1994 | Robinson et al. |
| 5,405,783 A | 4/1995 | Pirrung et al. |
| 5,445,934 A | 8/1995 | Fodor et al. |
| 5,468,846 A | 11/1995 | Ichikawa et al. |
| 5,488,567 A | 1/1996 | Allen et al. |
| 5,512,490 A | 4/1996 | Walt et al. |
| 5,532,138 A | 7/1996 | Singh et al. |
| 5,532,379 A | 7/1996 | Fujimoto |
| 5,545,531 A | 8/1996 | Rava et al. |
| 5,583,001 A | 12/1996 | Bobrow et al. |
| 5,620,850 A | 4/1997 | Bamdad et al. |
| 5,633,972 A | 5/1997 | Walt et al. |
| 5,690,894 A | 11/1997 | Pinkel et al. |
| 5,700,637 A | 12/1997 | Southern |
| 5,731,158 A | 3/1998 | Bobrow et al. |
| 5,770,455 A | 6/1998 | Cargill et al. |
| 5,807,522 A | 9/1998 | Brown et al. |
| 5,814,524 A | 9/1998 | Walt et al. |
| 5,885,529 A | 3/1999 | Babson et al. |
| 5,900,481 A | 5/1999 | Lough et al. |
| 5,981,180 A | 11/1999 | Chandler et al. |
| 6,001,564 A | 12/1999 | Bergeron et al. |
| 6,007,690 A | 12/1999 | Nelson et al. |
| 6,013,445 A | 1/2000 | Albrecht et al. |
| 6,023,540 A | 2/2000 | Walt et al. |
| 6,133,436 A | 10/2000 | Koster et al. |
| 6,143,496 A | 11/2000 | Brown et al. |
| 6,156,270 A | 12/2000 | Buechler |
| 6,174,695 B1 | 1/2001 | Hammock et al. |
| 6,210,910 B1 | 4/2001 | Walt et al. |
| 6,266,459 B1 | 7/2001 | Walt et al. |
| 6,285,807 B1 | 9/2001 | Walt et al. |
| 6,327,410 B1 | 12/2001 | Walt et al. |
| 6,329,139 B1 | 12/2001 | Nova et al. |
| 6,368,874 B1 | 4/2002 | Gallop et al. |
| 6,377,721 B1 | 4/2002 | Walt et al. |
| 6,388,746 B1 | 5/2002 | Eriksson et al. |
| 6,396,995 B1 | 5/2002 | Stuelpnagel et al. |
| 6,406,845 B1 | 6/2002 | Walt et al. |
| 6,432,630 B1 | 8/2002 | Blankenstein |
| 6,482,593 B2 | 11/2002 | Walt et al. |
| 6,582,908 B2 | 6/2003 | Fodor et al. |
| 6,602,702 B1 | 8/2003 | McDevitt et al. |
| 6,620,584 B1 * | 9/2003 | Chee ............ C07H 21/00 435/285.2 |
| 6,635,452 B1 | 10/2003 | Monforte et al. |
| 6,667,159 B1 | 12/2003 | Walt et al. |
| 6,713,309 B1 | 3/2004 | Anderson et al. |
| 6,714,303 B2 | 3/2004 | Ivarsson |
| 6,821,449 B2 | 11/2004 | Caplen et al. |
| 6,838,051 B2 | 1/2005 | Marquiss et al. |
| 6,858,394 B1 | 2/2005 | Chee et al. |
| 6,859,570 B2 | 2/2005 | Walt et al. |
| 6,878,345 B1 | 4/2005 | Astle |
| 6,929,924 B2 | 8/2005 | Bouanani et al. |
| 6,942,968 B1 | 9/2005 | Dickinson et al. |
| 6,943,034 B1 | 9/2005 | Winkler et al. |
| 6,991,939 B2 | 1/2006 | Walt et al. |
| 6,999,657 B2 | 2/2006 | Walt |
| 7,056,746 B2 | 6/2006 | Seul et al. |
| 7,060,431 B2 | 6/2006 | Chee et al. |
| 7,115,884 B1 | 10/2006 | Walt et al. |
| 7,211,390 B2 | 5/2007 | Rothberg et al. |
| 7,244,559 B2 | 7/2007 | Rothberg et al. |
| 7,250,267 B2 | 7/2007 | Walt et al. |
| 7,264,929 B2 | 9/2007 | Rothberg et al. |
| 7,348,181 B2 | 3/2008 | Walt et al. |
| 7,480,433 B2 | 1/2009 | Walt et al. |
| 7,572,581 B2 | 8/2009 | Gelfand et al. |
| 7,651,841 B2 | 1/2010 | Song et al. |
| 7,759,062 B2 | 7/2010 | Allawi et al. |
| 7,776,553 B2 | 8/2010 | Love et al. |
| 7,838,250 B1 | 11/2010 | Goix et al. |
| 8,222,047 B2 | 7/2012 | Duffy et al. |
| 8,236,574 B2 | 8/2012 | Duffy et al. |
| 8,415,171 B2 | 4/2013 | Rissin et al. |
| 8,460,878 B2 | 6/2013 | Walt et al. |
| 8,460,879 B2 | 6/2013 | Walt et al. |
| 8,492,098 B2 | 7/2013 | Walt et al. |
| 8,846,415 B2 | 9/2014 | Duffy et al. |
| 9,110,025 B2 | 8/2015 | Rissin et al. |
| 9,310,360 B2 | 4/2016 | Duffy et al. |
| 9,395,359 B2 | 7/2016 | Walt et al. |
| 9,482,622 B2 | 11/2016 | Sato et al. |
| 9,482,662 B2 | 11/2016 | Duffy et al. |
| 9,551,663 B2 | 1/2017 | Rissin et al. |
| 9,678,068 B2 | 6/2017 | Duffy et al. |
| 9,809,838 B2 | 11/2017 | Walt et al. |
| 9,846,155 B2 | 12/2017 | Rissin et al. |
| 9,932,626 B2 | 4/2018 | Duffy et al. |
| 9,952,237 B2 | 4/2018 | Fournier et al. |
| 10,261,089 B2 | 4/2019 | Walt et al. |
| 10,393,759 B2 | 8/2019 | Wilson et al. |
| 10,640,814 B2 | 5/2020 | Duffy et al. |
| 10,725,032 B2 | 7/2020 | Duffy et al. |
| 2002/0009391 A1 | 1/2002 | Marquiss et al. |
| 2002/0090650 A1 | 7/2002 | Empedocles et al. |
| 2002/0122612 A1 | 9/2002 | Walt et al. |
| 2003/0027126 A1 | 2/2003 | Walt et al. |
| 2003/0091475 A1 | 5/2003 | Yu et al. |
| 2003/0096227 A1 | 5/2003 | Shinitzky et al. |
| 2003/0096243 A1 | 5/2003 | Busa |
| 2003/0104361 A1 | 6/2003 | Weininger et al. |
| 2003/0143580 A1 | 7/2003 | Straus et al. |
| 2003/0198573 A1 | 10/2003 | Forood et al. |
| 2004/0018561 A1 | 1/2004 | Decrescenzo et al. |
| 2004/0038426 A1 | 2/2004 | Manalis |
| 2004/0043502 A1 | 3/2004 | Song et al. |
| 2004/0053322 A1 | 3/2004 | McDevitt et al. |
| 2004/0071599 A1 | 4/2004 | Rusch et al. |
| 2004/0072278 A1 | 4/2004 | Chou et al. |
| 2004/0086426 A1 | 5/2004 | Vann et al. |
| 2004/0101918 A1 | 5/2004 | Cauci |
| 2004/0142386 A1 | 7/2004 | Rigler et al. |
| 2004/0248325 A1 | 12/2004 | Bukusoglu |
| 2004/0253624 A1 | 12/2004 | Smith et al. |

(56) References Cited

U.S. PATENT DOCUMENTS

| | | |
|---|---|---|
| 2004/0259237 A1 | 12/2004 | Kellogg et al. |
| 2005/0053996 A1 | 3/2005 | Tong |
| 2005/0112634 A1 | 5/2005 | Woudenberg et al. |
| 2005/0112655 A1 | 5/2005 | Banerjee et al. |
| 2005/0129581 A1 | 6/2005 | McBride et al. |
| 2005/0130173 A1 | 6/2005 | Leamon et al. |
| 2005/0130188 A1 | 6/2005 | Walt et al. |
| 2005/0131650 A1 | 6/2005 | Andersson et al. |
| 2005/0164289 A1 | 7/2005 | Quate et al. |
| 2005/0221281 A1 | 10/2005 | Ho |
| 2005/0226780 A1 | 10/2005 | Sandell et al. |
| 2005/0244308 A1 | 11/2005 | Tanaami et al. |
| 2005/0266433 A1 | 12/2005 | Kapur et al. |
| 2006/0006067 A1 | 1/2006 | Unger |
| 2006/0013543 A1 | 1/2006 | Walt et al. |
| 2006/0040297 A1 | 2/2006 | Leamon et al. |
| 2006/0068409 A1 | 3/2006 | Phan et al. |
| 2006/0078998 A1 | 4/2006 | Puskas et al. |
| 2006/0084183 A1 | 4/2006 | Henricksen |
| 2006/0139635 A1 | 6/2006 | Kersey et al. |
| 2007/0040095 A1 | 2/2007 | Walt et al. |
| 2007/0059754 A1 | 3/2007 | Kordunsky et al. |
| 2007/0074972 A1 | 4/2007 | Nassef et al. |
| 2007/0116607 A1 | 5/2007 | Wang et al. |
| 2007/0259381 A1 | 11/2007 | Rissin et al. |
| 2007/0259385 A1 | 11/2007 | Rissin et al. |
| 2007/0259448 A1 | 11/2007 | Rissin et al. |
| 2008/0032324 A1 | 2/2008 | Walt et al. |
| 2008/0039343 A1 | 2/2008 | Guire et al. |
| 2008/0064113 A1 | 3/2008 | Goix et al. |
| 2008/0254482 A1 | 10/2008 | Mattoon et al. |
| 2008/0269069 A1 | 10/2008 | Bacher et al. |
| 2009/0036324 A1 | 2/2009 | Fan et al. |
| 2009/0087860 A1 | 4/2009 | Todd et al. |
| 2009/0142755 A1 | 6/2009 | Albitar |
| 2009/0149341 A1 | 6/2009 | Walt et al. |
| 2009/0156425 A1 | 6/2009 | Walt et al. |
| 2009/0170728 A1 | 7/2009 | Walt et al. |
| 2009/0239308 A1 | 9/2009 | Dube et al. |
| 2009/0254180 A1 | 10/2009 | Pazanowski et al. |
| 2009/0289834 A1 | 11/2009 | Devensky |
| 2009/0307772 A1 | 12/2009 | Markham et al. |
| 2010/0075355 A1 | 3/2010 | Duffy et al. |
| 2010/0075407 A1 | 3/2010 | Duffy et al. |
| 2010/0075439 A1 | 3/2010 | Duffy et al. |
| 2010/0075862 A1 | 3/2010 | Duffy et al. |
| 2010/0140289 A1 | 6/2010 | Knobel et al. |
| 2010/0189338 A1 | 7/2010 | Lin et al. |
| 2010/0192573 A1 | 8/2010 | Hamilton et al. |
| 2010/0204335 A1 | 8/2010 | Beddingfield et al. |
| 2010/0225913 A1 | 9/2010 | Trainer |
| 2010/0227379 A1 | 9/2010 | Wo et al. |
| 2010/0329929 A1 | 12/2010 | Goix et al. |
| 2011/0037463 A1 | 2/2011 | Bertacco et al. |
| 2011/0183330 A1 | 7/2011 | Lo et al. |
| 2011/0195852 A1 | 8/2011 | Walt et al. |
| 2011/0212462 A1 | 9/2011 | Duffy et al. |
| 2011/0212537 A1 | 9/2011 | Rissin et al. |
| 2011/0212848 A1 | 9/2011 | Duffy et al. |
| 2011/0245097 A1 | 10/2011 | Rissin et al. |
| 2012/0183967 A1 | 7/2012 | Dressman et al. |
| 2012/0196774 A1 | 8/2012 | Fournier et al. |
| 2012/0214160 A1 | 8/2012 | Deng et al. |
| 2012/0277114 A1 | 11/2012 | Duffy et al. |
| 2012/0289428 A1 | 11/2012 | Duffy et al. |
| 2013/0165342 A1 | 6/2013 | Rissin et al. |
| 2013/0345078 A1 | 12/2013 | Walt et al. |
| 2014/0094386 A1 | 4/2014 | Wilson et al. |
| 2014/0227720 A1 | 8/2014 | Wilson et al. |
| 2014/0302532 A1 | 10/2014 | Wilson et al. |
| 2015/0233905 A1 | 8/2015 | Walt et al. |
| 2015/0353997 A1 | 12/2015 | Duffy et al. |
| 2015/0355182 A1 | 12/2015 | Rissin et al. |
| 2016/0123969 A1 | 5/2016 | Rissin et al. |
| 2016/0258959 A1 | 9/2016 | Wilson et al. |
| 2017/0038390 A1 | 2/2017 | Walt et al. |
| 2017/0159104 A1 | 6/2017 | Walt et al. |
| 2017/0160292 A1 | 6/2017 | Wilson et al. |
| 2018/0003703 A1 | 1/2018 | Duffy et al. |
| 2018/0017552 A1 | 1/2018 | Duffy et al. |
| 2018/0224451 A1 | 8/2018 | Rissin et al. |
| 2018/0306830 A1 | 10/2018 | Fournier et al. |
| 2018/0363038 A1 | 12/2018 | Duffy et al. |
| 2019/0302109 A1 | 10/2019 | Duffy et al. |
| 2020/0123592 A1 | 4/2020 | Díaz-Mochón et al. |
| 2020/0124620 A1 | 4/2020 | Wilson et al. |
| 2020/0271643 A1 | 8/2020 | Wilson et al. |

FOREIGN PATENT DOCUMENTS

| | | |
|---|---|---|
| CN | 1950520 A | 4/2007 |
| CN | 101351564 A | 1/2009 |
| CN | 101529227 A | 9/2009 |
| CN | 101541974 A | 9/2009 |
| DE | 19540098 A1 | 4/1997 |
| EP | 0 805 215 A2 | 11/1997 |
| EP | 1 180 679 A1 | 2/2002 |
| EP | 1 259 810 B1 | 11/2006 |
| EP | 1 721 657 A1 | 11/2006 |
| EP | 2 267 451 A2 | 12/2010 |
| JP | 2001-269196 A | 10/2001 |
| JP | 2002-506200 A | 2/2002 |
| JP | 2002-525587 A | 8/2002 |
| JP | 2002-526743 A | 8/2002 |
| JP | 2004-354164 A | 12/2004 |
| JP | 2005-518553 A | 6/2005 |
| JP | 2006-511792 A | 4/2006 |
| WO | WO 88/05533 A1 | 7/1988 |
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |
| WO | WO 99/58948 A2 | 11/1999 |
| WO | WO 00/04372 A1 | 1/2000 |
| WO | WO 00/47996 A2 | 8/2000 |
| WO | WO 01/57520 A2 | 8/2001 |
| WO | WO 02/077646 A1 | 10/2002 |
| WO | WO 03/054142 A2 | 7/2003 |
| WO | WO 03/073817 A1 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2005/095262 A1 | 10/2005 |
| WO | WO 2006/007726 A1 | 1/2006 |
| WO | WO 2006/055739 A2 | 5/2006 |
| WO | WO 2006/078289 A2 | 7/2006 |
| WO | WO 2006/102297 A1 | 9/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |
| WO | WO 2011/109364 A2 | 9/2011 |
| WO | WO 2011/109372 A1 | 9/2011 |
| WO | WO 2016/115256 A1 | 7/2016 |
| WO | WO 2016/130923 A1 | 8/2016 |

(56) References Cited

FOREIGN PATENT DOCUMENTS

| WO | WO 2018/222585 A2 | 12/2018 |
|---|---|---|
| WO | WO 2019/060607 A1 | 3/2019 |

OTHER PUBLICATIONS

International Search Report and Written Opinion for International Application No. PCT/US2007/019184, dated Jun. 19, 2008.
International Preliminary Report on Patentability, Chapter 1, for International Application No. PCT/US2007/019184, dated Mar. 11, 2010.
European Search Report for European Application No. 07751131.9, dated Sep. 8, 2009.
Extended European Search Report for European Application No. 12177276.8 dated Nov. 26, 2012.
International Search Report and Written Opinion for International Application No. PCT/US2007/004349, dated Aug. 21, 2008.
International Preliminary Report on Patentability, Chapter 1, for International Application No. PCT/US2007/004349 dated Sep. 25, 2008.
International Preliminary Report on Patentability, Chapter 2, for International Application No. PCT/US2007/004349 dated Mar. 23, 2009.
Office Communication for CA Application No. 2,734,029, filed Aug. 7, 2007, which Office Communication is dated Oct. 1, 2013, and claims as pending for Canadian Application No. 2,734,029.
Office Communication for CA Application No. 2,734,029, filed Aug. 7, 2007, which Office Communication is dated Aug. 5, 2014, and claims as pending for Canadian Application No. 2,734,029 as of Apr. 1, 2014.
Office Communication for EP Application No. 07837608.4 filed Aug. 30, 2007, published as EP 2201374 on Jun. 30, 2010, which Office Communication is dated May 6, 2010, and claims as pending for EP Application No. 07837608.4 as of May 6, 2010.
Response to Office Communication for EP Application No. 07837608.4 filed Aug. 30, 2007, published as EP 2201374 on Jun. 30, 2010, which Response is dated Jun. 15, 2010, and claims as pending for EP Application No. 07837608.4 as of Jun. 15, 2010.
Office Communication for EP Application No. 07837608.4 filed Aug. 30, 2007, published as EP 2201374 on Jun. 30, 2010, which Office Communication is dated Dec. 1, 2010, and claims as pending for EP Application No. 07837608.4 as of Dec. 1, 2010.
Response to Office Communication for EP Application No. 07837608.4 filed Aug. 30, 2007, published as EP 2201374 on Jun. 30, 2010, which Response is dated Jun. 9, 2011, and claims as pending for EP Application No. 07837608.4 as of Jun. 9, 2011.
Office Communication for EP Application No. 07837608.4 filed Aug. 30, 2007, published as EP 2201374 on Jun. 30, 2010, which Office Communication is dated Dec. 12, 2011, and claims as pending for EP Application No. 07837608.4 as of Dec. 12, 2011.
Office Communication for EP Application No. 07837608.4, filed Aug. 30, 2007, published as EP 2201374, which Office Communication is dated Sep. 6, 2012, and claims as pending for EP Application No. 07837608.4 as of Sep. 6, 2012.
Office Communication for EP Application No. 07837608.4, filed Aug. 30, 2007, which Office Communication is dated Jan. 16, 2014, and claims as pending for EP Application No. 07837608.4 as of May 14, 2013.
Office Communication for EP Application No. 07837608.4, filed Aug. 30, 2007, which Office Communication is dated Sep. 16, 2014, and claims as pending for EP Application No. 07837608.4 as of Jul. 28, 2014.
Translation of Office Action for Japanese Application No. 2010-522877 filed Aug. 30, 2007, which Office Action is dated Jan. 17, 2012, and translation of claims as pending for Japanese Application No. 2010-522877 as of Jan. 17, 2012.
Decision to Grant for Japanese Application No. 2010-522877 filed Aug. 30, 2007, which Office Action is dated Feb. 18, 2014, and translation of claims as pending for Japanese Application No. 2010-522877 as of Jun. 5, 2013.
Office Communication for U.S. Appl. No. 12/675,686, filed Apr. 4, 2011, which Office Communication is dated Nov. 30, 2015, and claims as pending for U.S. Appl. No. 12/675,686 as of Sep. 3, 2015.
Office Communication for EP Application No. 07751131.9 filed Feb. 20, 2007, published as EP 1996717 on Dec. 3, 2008, which Office Communication is dated Oct. 30, 2008, and claims as pending for EP Application No. 07837608.4 as of Oct. 30, 2008.
Response to Office Communication for EP Application No. 07751131.9 filed Feb. 20, 2007, published as EP 1996717 on Dec. 3, 2008, which Response is dated Dec. 9, 2008, and claims as pending for EP Application No. 07751131.9 as of Dec. 9, 2008.
Office Communication for EP Application No. 07751131.9 filed Feb. 20, 2007, published as EP 1996717 on Dec. 3, 2008, which Office Communication is dated Sep. 8, 2009, and claims as pending for EP Application No. 07837608.4 as of Sep. 8, 2009.
Response to Office Communication for EP Application No. 07751131.9 filed Feb. 20, 2007, published as EP 1996717 on Dec. 3, 2008, which Response is dated Dec. 10, 2009, and claims as pending for EP Application No. 07751131.9 as of Dec. 10, 2009.
Office Communication for EP Application No. 07751131.9 filed Feb. 20, 2007, published as EP 1996717 on Dec. 3, 2008, which Office Communication is dated Jul. 20, 2010, and claims as pending for EP Application No. 07837608.4 as of Jul. 20, 2010.
Response to Office Communication for EP Application No. 07751131.9 filed Feb. 20, 2007, published as EP 1996717 on Dec. 3, 2008, which Response is dated Jan. 19, 2011, and claims as pending for EP Application No. 07751131.9 as of Jan. 19, 2011.
Office Communication for EP Application No. 07751131.9 filed Feb. 20, 2007, published as EP 1996717 on Dec. 3, 2008, which Office Communication is dated Nov. 30, 2011, and claims as pending for EP Application No. 07837608.4 as of Nov. 30, 2011.
Office Communication for EP Application No. 07751131.9, filed Feb. 20, 2007, which Office Action is dated Mar. 28, 2013, and claims as allowed for European Application No. 07751131.9 as of Mar. 28, 2013.
Office Communication for EP Application No. 07751131.9, filed Feb. 20, 2007, which Office Action is dated Apr. 5, 2013, and claims as allowed for European Application No. 07751131.9 as of Apr. 5, 2013.
Intention to Grant for EP Application No. 07751131.9, filed Feb. 20, 2007, which Intention to Grant is dated May 27, 2014, and claims as allowed for European Application No. 07751131.9 as of Aug. 2, 2013.
Office Communication for EP Application No. 12177276.8, filed Feb. 20, 2007, which Office Communication is dated Nov. 26, 2012, and claims as pending for EP Application No. 12177276.8 as of Nov. 26, 2012.
Office Communication for EP Application No. 12177276.8, filed Feb. 20, 2007, which Office Action is dated Apr. 28, 2014, and claims as allowed for European Application No. 12177276.8 as of Jun. 26, 2013.
Office Communication for EP Application No. 12177276.8, filed Feb. 20, 2007, which Office Communication is dated Dec. 23, 2014, and claims as pending for EP Application No. 12177276.8 as of Sep. 8, 2014.
Decision to Grant for EP Application No. 12177276.8, filed Feb. 20, 2007, which Decision to Grant is dated Jan. 29, 2016, and claims as granted for EP Application No. 12177276.8.
Office Communication for JP Application No. 2011-034007, filed Feb. 20, 2007, which Office Action is dated May 19, 2013, and claims as pending for Japanese Application No. 2011-034007 as of Feb. 19, 2013.
Decision to Grant for JP Application No. 2011-034007, filed Feb. 20, 2007, which Decision to Grant is dated Oct. 8, 2013, and claims as allowed for Japanese Application No. 2011-034007.
Office Action for U.S. Appl. No. 11/707,385, filed Feb. 16, 2007, published as US 2007-0259448 on Nov. 8, 2007, which Office Action is dated Mar. 16, 2009, and claims as pending for U.S. Appl. No. 11/707,385 as of Mar. 16, 2009.
Office Action for U.S. Appl. No. 11/707,385, filed Feb. 16, 2007, published as US 2007-0259448 on Nov. 8, 2007, which Office Action is dated Jan. 26, 2010, and claims as pending for U.S. Appl. No. 11/707,385 as of Jan. 26, 2010.

(56) References Cited

OTHER PUBLICATIONS

Office Action for U.S. Appl. No. 11/707,385, filed Feb. 16, 2007, published as US 2007-0259448 on Nov. 8, 2007, which Office Action is dated Sep. 27, 2012, and claims as pending for U.S. Appl. No. 11/707,385 as of Sep. 27, 2012.
Notice of Allowance for U.S. Appl. No. 11/707,385, filed Feb. 16, 2007, published as US-2007-0259448 on Nov. 8, 2007, which Notice of Allowance is dated Feb. 25, 2013, and claims as allowed for Office Action for U.S. Appl. No. 11/707,385 as of Feb. 25, 2013.
Office Action for U.S. Appl. No. 11/707,383, filed Feb. 16, 2007, published as US 2007-0259385 on Nov. 8, 2007, which Office Action is dated Mar. 16, 2009, and claims as pending for U.S. Appl. No. 11/707,383 as of Mar. 16, 2009.
Office Action for U.S. Appl. No. 11/707,383, filed Feb. 16, 2007, published as US 2007-0259385 on Nov. 8, 2007, which Office Action is dated Nov. 27, 2009, and claims as pending for U.S. Appl. No. 11/707,383 as of Nov. 27, 2009.
Office Action for U.S. Appl. No. 11/707,383, filed Feb. 16, 2007, published as US 2007-0259385 on Nov. 8, 2007, which Office Action is dated Sep. 27, 2012, and claims as pending for U.S. Appl. No. 11/707,383 as of Sep. 27, 2012.
Notice of Allowance for U.S. Appl. No. 11/707,383, filed Feb. 16, 2007, published as US 2007-0259385 on Nov. 8, 2007, which Office Action is dated Feb. 8, 2013, and claims as allowed for U.S. Appl. No. 11/707,383 as of Feb. 8, 2013.
[No Author Listed], bioMérieux and Quanterix Sign Strategic Partnership in Ultrasensitive and Multiplex Immunoassays. Quanterix Press Release. Nov. 15, 2012. 2 pages.
[No Author Listed], Does Brain Hypoxia Help Kick Off Alzheimer's Pathology? Alzheimer Research Forum. Dec. 16, 2011. http://www.alzforum.org/new/detailprint.asp?id=3002 [last accessed Jan. 30, 2012]. 4 pages.
[No Author Listed], Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.
[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last accessed Jan. 31, 2012]. 2 pages.
[No Author Listed], Quanterix and STRATEC Announce Strategic Partnership. Quanterix Press Release. Aug. 16, 2011. 2 pages.
[No Author Listed], Quanterix Announces Commercial Availability of its Simoa Single Molecule Array Technology. Quanterix Press Release. Jul. 30, 2013. 2 pages.
[No Author Listed], Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.
[No Author Listed], Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.
[No Author Listed], Quanterix Launches Multiplexed Single Molecule Immunoassay Technology to Improve Diagnosis and Potential Treatment of Complex Diseases. Quanterix Press Release. Sep. 17, 2013. 2 pages.
[No Author Listed], Quanterix to Present Poster Session on Blood-based Brain Biomarker Measurements of Sports Related Brain Injury at Neuroscience. Quanterix Press Release. Nov. 4, 2013. 1 page.
[No Author Listed], Quanterix's Simoa technology to detect blood biomarker for concussion in hockey players. Quanterix Press Release. Mar. 14, 2014. 1 page.
[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.
[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.
[No Author Listed], Single molecule arrays for digital detection in complex samples. Quanterix Corporation. IQT Technology Focus Day. Mar. 25, 2010. PowerPoint presentation. 30 pages.
Adams et al., Encoded fiber-optic microsphere arrays for probing protein-carbohydrate interactions. Angewandte Chemie. 2003; 115:5475-5478.
Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.
Agrawal et al., Single-bead immunoassays using magnetic microparticles and spectral-shifting quantum dots. *J Agric Food Chem*. May 16, 2007; 55(10):3778-82. Epub Apr. 25, 2007.
Ahn et al., Detection of *Salmonella* spp. Using microsphere-based, fiber-optic DNA microarrays. Anal Chem. Aug. 1, 2005; 77(15):5041-7.
Ahn et al., Fiber-optic microarray for simultaneous detection of multiple harmful algal bloom species. Appl Environ Microbiol. Sep. 2006; 72(9):5742-9.
Albert et al., Automatic decoding of sensor types within randomly ordered, high-density optical sensor arrays. *Anal Bioanal Chem*. Apr. 2002; 373(8):792-802. Epub Jul. 27, 2002.
Albert et al., Cross-reactive chemical sensor arrays. *Chem Rev*. Jul. 12, 2000; 100(7):2595-626.
Albert et al., Information coding in artificial olfaction multisensor arrays. Anal Chem. Aug. 15, 2003; 75(16):4161-7.
Albert et al., Optical multibead arrays for simple and complex odor discrimination. *Anal Chem*. Jun. 1, 2001; 73(11):2501-8.
Angenendt et al., Subnanoliter enzymatic assays on microarrays. Proteomics. Feb. 2005;5(2):420-5.
Arnaud, Observing single enzymes at work. Chemical & Engineering News. Oct. 2007; 85(44): 8.
Beer et al., On-chip, real-time, single-copy polymerase chain reaction in picoliter droplets. Anal Chem. Nov. 15, 2007;79(22):8471-5. Epub Oct. 11, 2007. Abstract only.
Bencic-Nagale et al., Extending the longevity of fluorescence-based sensor arrays using adaptive exposure. Anal Chem. Oct. 1, 2005; 77(19):6155-62.
Bhat et al., Single molecule detection in nanofluidic digital array enables accurate measurement of DNA copy number. Anal Bioanal Chem. May 2009;394(2):457-67. Epub Mar. 15, 2009.
Biran et al., Optical imaging fiber-based live bacterial cell array biosensor. *Anal Biochem*. Apr. 1, 2003;315(1):106-13.
Biran et al., Optical imaging fiber-based single live cell arrays: a high-density cell assay platform. *Anal Chem*. Jul. 1, 2002; 74(13):3046-54.
Blake et al., Phenotypic consequences of promoter-mediated transcriptional noise. Mol Cell. Dec. 28, 2006; 24(6):853-65.
Blicharz et al., Detection of inflammatory cytokines using a fiber optic microsphere immunoassay array. *Proc. SPIE*. 2006; 6380, 638010-1-638010-6.
Blicharz et al., Fiber-optic microsphere-based antibody array for the analysis of inflammatory cytokines in saliva. Anal. Chem. 2009;81(6):2106-14.
Blicharz et al., Use of colorimetric test strips for monitoring the effect of hemodialysis on salivary nitrite and uric acid in patients with end-stage renal disease: a proof of principle. Clin Chem. Sep. 2008; 54(9): 1473-80. Epub Aug. 1, 2008.
Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.
Bowden et al., Development of a microfluidic platform with an optical imaging microarray capable of attomolar target DNA detection. Anal Chem. Sep. 1, 2005; 77(17):5583-8. Epub Aug. 4, 2005.
Boyden, The chemotactic effect of mixtures of antibody and antigen on polymorphonuclear leucocytes. J Exp Med. Mar. 1, 1962;115:453-66.
Brehm-Stecher et al., Single-cell microbiology: tools, technologies, and applications. *Microbiol Mol Biol Rev*. Sep. 2004; 68(3):538-59.

(56) References Cited

OTHER PUBLICATIONS

Brogan et al., Optical fiber-based sensors: application to chemical biology. Curr Opin Chem Biol. Oct. 2005; 9(5):494-500. Epub Aug. 24, 2005.
Bronk et al., Combined imaging and chemical sensing using a single optical imaging fiber. *Anal Chem*. Sep. 1, 1995; 67(17):2750-7.
Bronk et al., Fabrication of patterned sensor arrays with aryl azides on a polymer-coated imaging optical fiber bundle. *Anal Chem*. Oct. 15, 1994; 66(20):3519-20.
Burton et al., A microfluidic chip-compatible bioassay based on single-molecule detection with high sensitivity and multiplexing. *Lab Chip*. Apr. 7, 2010; 10(7):843-51. Epub Jan. 14, 2010.
Campian, Colored and fluorescent solid supports. Innovation and Perspectives in Solid Phase Synthesis. Ed. R. Epton, Mayflower Worldwide Limited, Birmingham. Ch. 77. 1994:469-472.
Chen et al., Microfabricated arrays of cylindrical wells facilitate single-molecule enzymology of alpha-chymotrypsin. *Biotechnol Prog*. Jul.-Aug. 2009; 25(4):929-37.
Chin et al., Editor's Choice: Distinctive individualism. Science. Apr. 4, 2008;320:21.
Chon et al., Characterization of single-cell migration using a computer-aided fluorescence time-lapse videomicroscopy system. Anal Biochem. Oct. 15, 1997;252(2):246-54.
Deutsch et al., Apparatus for high-precision repetitive sequential optical measurement of living cells. *Cytometry*. Jul. 1, 1994; 16(3):214-26.
Dicesare et al., Individual cell migration analysis using fiber-optic bundles. Anal Bioanal Chem. May 2005; 382(1):37-43. Epub Apr. 1, 2005.
Dickinson et al., A chemical-detecting system based on a cross-reactive optical sensor array. *Nature*. Aug. 22, 1996; 382(6593):697-700.
Dickinson et al., Convergent, self-encoded bead sensor arrays in the design of an artificial. *Anal Chem*. Jun. 1, 1999; 71(11):2192-8.
Dickinson et al., Current trends in 'artificial-nose' technology. *Trends Biotechnol*. Jun. 1998; 16(6):250-8.
Duffy et al., Detection of prostate specific antigen (PSA) in the serum of radical prostatectomy patients at femtogram per milliliter levels using digital ELISA (AccuPSA™) based on single molecule arrays (SiMoA). AACC Meeting Poster. 2010. 1 page.
Duffy, Immunoassays with Broad Dynamic Ranges based on Combining Digital and Digitally Enhanced Analog Detecion of Enzyme Labels. Oak Ridge Conference. Presentation. Apr. 15, 2011. 16 pages.
Duffy, Single Molecule Arrays (Simoa) for Ultrasensitive Protein Detection in Companion Diagnostics. Next Generation DX Summit. Aug. 22, 2012. PowerPoint presentation.
Egner et al., Tagging in combinatorial chemistry: the use of coloured and flurorescent beads. ChemCommun. 1997; 735-736.
Eid et al., Real-time DNA sequencing from single polymerase molecules. *Science*. Jan. 2, 2009; 323(5910):133-8. Epub Nov. 20, 2008.
Ekins et al., Single-molecule ELISA. Clin Chem. Mar. 2011;57(3):372-5. Epub Oct. 13, 2010. Papers in press. Oct. 13, 2010. pp. 1-3.
English et al., Ever-fluctuating single enzyme molecules: Michaelis-Menten equation revisited. *Nat Chem Biol*. Feb. 2006; 2(2):87-94. Epub Dec. 25, 2005.
Epstein et al., Combinatorial decoding: an approach for universal DNA array fabrication. *J Am Chem Soc*. Nov. 12, 2003; 125(45):13753-9.
Epstein et al., *Fluorescence-based nucleic acid detection and microarrays*. Analytica Chimica. Acta. 2002; 469:3-36.
Epstein et al., High-density fiber-optic genosensor microsphere array capable of zeptomole detection limits. *Anal Chem*. Apr. 15, 2002; 74(8):1836-40.
Epstein et al., High-density, microsphere-based fiber optic DNA microarrays. *Biosens Bioelectron*. May 2003; 18(5-6):541-6.
Epstein, et al., Fluorescence-based fibre optic arrays: a universal platform for sensing. *Chem Soc Rev*. Jul. 2003; 32(4):203-14.

Ferguson et al., A fiber-optic DNA biosensor microarray for the analysis of gene expression. *Nat Biotechnol*. Dec. 1996; 14(13):1681-4.
Ferguson et al., High-density fiber-optic DNA random microsphere array. *Anal Chem*. Nov. 15, 2000; 72(22):5618-24.
Ferguson et al., Simultaneous monitoring of pH, $CO_2$ and $O_2$ using an optical imaging fiber. Analytica Chimica Acta. 1997; 340(1-3): 123-131.
Fister et al., Counting single chromophore molecules for ultrasensitive analysis and separations on microchip devices. Analytical Chemistry. 1998; 70:431-437.
Fulton et al., Advanced multiplexed analysis with the FlowMetrix system. *Clin Chem*. Sep. 1997; 43(9):1749-56.
Furka et al., General method for rapid synthesis of multicomponent peptide mixtures. Int J Pept Protein Res. Jun. 1991;37(6):487-93.
Gebel, Molecule counting made easy. Anal Chem. Sep. 1, 2009; 7130-7131.
Giaever et al., Micromotion of mammalian cells measured electrically. Proc Natl Acad Sci U S A. Sep. 1, 1991;88(17):7896-900.
Gorris et al., Analytical chemistry on the femtoliter scale. Angew Chem Int Ed. 2010; 49:2-18.
Gorris et al., Mechanistic aspects of horseradish peroxidase elucidated through single-molecule studies. *J Am Chem Soc*. May 6, 2009; 131(17):6277-82.
Gorris et al., Optical-fiber bundles. FEBS J. Nov. 2007; 274(21):5462-70. Epub Oct. 12, 2007.
Gorris et al., Stochastic inhibitor release and binding from single-enzyme molecules. *Proc Natl Acad Sci U S A*. Nov. 6, 2007; 104(45): 17680-5. Epub Oct. 26, 2007.
Härma et al., Europium nanoparticles and time-resolved fluorescence for ultrasensitive detection of prostate-specific antigen. *Clin Chem*. Mar. 2001; 47(3):561-8.
Härma et al., Miniature single-particle immunoassay for prostate-specific antigen in serum using recombinant Fab fragments. *Clin Chem*. Nov. 2000; 46(11):1755-61.
Härma et al., Zeptomole detection sensitivity of prostate-specific antigen in a rapid microtitre plate assay using time-resolved fluorescence. *Luminescence*. Nov.-Dec. 2000;15(6):351-5.
Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. *Clin Diagn Lab Immunol*. Sep. 1995; 2(5):535-41.
Haugland, Handbook: A Guide to Fluorescent Probes and Labeling Technologies. Invitrogen, Eugene, OR. Molecular Probes, US. pp. 473-538.
He et al., Selective encapsulation of single cells and subcellular organelles into picoliter- and femtoliter-volume droplets. *Anal Chem*. Mar. 15, 2005; 77(6):1539-44.
Healey et al., Fiberoptic DNA sensor array capable of detecting point mutations. *Anal Biochem*. Sep. 5, 1997; 251(2):270-9.
Healey et al., Multianalyte biosensors on optical imaging bundles. *Biosens Bioelectron*. 1997; 12(6):521-9.
Healey et al., Photodeposition of micrometer-scale polymer patterns on optical imaging fibers. Science. Aug. 25, 1995; 269(5227):1078-80.
Hindson et al., High-throughput droplet digital PCR system for absolute quantitation of DNA copy number. Anal Chem. Nov. 15, 2011;83(22):8604-10. Epub Oct. 28, 2011.
Hirano et al., A novel method for DNA molecular counting. Nucleic Acids Symp Ser. 2000;(44):157-8.
Hirschfeld, Remote and in-situ analysis. Anal Chem. 1986; 324:618-624.
Hunsaker et al., Nucleic acid hybridization assays employing dA-tailed capture probes. II. Advanced multiple capture methods. *Anal Biochem*. Sep. 1989; 181(2):360-70.
Johnson et al., Identification of multiple analytes using an optical sensor array and pattern recognition neural networks. Analytical Chemistry. 1997; 69(22):4641-8.
Kiss et al., High-throughput quantitative polymerase chain reaction in picoliter droplets. Anal Chem. Dec. 1, 2008;80(23):8975-81.

(56) References Cited

OTHER PUBLICATIONS

Kremsky et al., Immobilization of DNA via oligonucleotides containing an aldehyde or carboxylic acid group at the 5' terminus. *Nucleic Acids Res.* Apr. 10, 1987; 15(7):2891-909.

Kuang et al., Living bacterial cell array for genotoxin monitoring. *Anal Chem.* May 15, 2004; 76(10):2902-9.

Kuang et al., Monitoring "promiscuous" drug effects on single cells of multiple cell types. *Anal Biochem.* Oct. 15, 2005; 345(2):320-5.

Kuang et al., Simultaneously monitoring gene expression kinetics and genetic noise in single cells by optical well arrays. *Anal Chem.* Nov. 1, 2004; 76(21):6282-6.

Lafratta et al., Very high density sensing arrays. Chem Rev. Feb. 2008; 108(2):614-37. Epub Jan. 30, 2008.

Lee et al., A fiber-optic microarray biosensor using aptamers as receptors. *Anal Biochem.* Jun. 15, 2000; 282(1):142-6.

Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.

Li et al., Molecule by molecule direct and quantitative counting of antibody-protein complexes in solution. *Anal Chem.* Aug. 1, 2004; 76(15):4446-51.

Lu et al., Single-molecule enzymatic dynamics. *Science.* Dec. 4, 1998; 282(5395):1877-82.

Luo et al., Single-molecule and ensemble fluorescence assays for a functionally important conformational change in T7 DNA polymerase. *Proc Natl Acad Sci U S A.* Jul. 31, 2007; 104(31):12610-5. Epub Jul. 18, 2007.

Melin et al., Microfluidic large-scale integration: the evolution of design rules for biological automation. *Annu Rev Biophys Biomol Struct.* 2007; 36:213-31.

Michael et al., Combined imaging and chemical sensing of fertilization-induced acid release from single sea urchin eggs. *Anal Biochem.* Sep. 10, 1999; 273(2):168-78.

Michael et al., Randomly ordered addressable high-density optical sensor arrays. *Anal Chem.* Apr. 1, 1998; 70(7):1242-8.

Monk et al., Fabrication of gold microtubes and microwires in high aspect ratio capillary arrays. *J Am Chem Soc.* Sep. 22, 2004; 126(37):11416-7.

Monk et al., Optical fiber-based biosensors. *Anal Bioanal Chem.* Aug. 2004; 379(7-8):931-45. Epub Jun. 23, 2004.

Monk et al., Progress toward the dermination of $Sr^{2+}$ in highly basic solutions using imagining optical fiber sensor arrays. J. Mater. Chem. 2005; 15:4361-4366.

Morrison et al., Nanoliter high throughput quantitative PCR. Nucleic Acids Res. 2006;34(18):e123. Epub Sep. 25, 2006.

Munkholm et al., Polymer modification of fiber optic chemical sensors as a method of enhancing fluroescence signal for pH measurement. Anal Chem. 1986; 58:1427-1430.

Nagai et al., High-throughput PCR in silicon based microchamber array. *Biosens Bioelectron.* Dec. 2001; 16(9-12):1015-9.

Nalefski et al., Single-molecule detection for femtomolar quantification of proteins in heterogeneous immunoassays. *Clin Chem.* Nov. 2006; 52(11):2172-5.

Nam et al., Nanoparticle-based bio-bar codes for the ultrasensitive detection of proteins. *Science.* Sep. 26, 2003;301(5641):1884-6.

Niemeyer et al., Combination of DNA-directed immobilization and immuno-PCR: very sensitive antigen detection by means of self-assembled DNA-protein conjugates. *Nucleic Acids Res.* Aug. 15, 2003; 31(16):e90, 7 pages.

Okrongly, Single Molecule Enzyme Detection and Application to Immunoassay: Implications for Personalized Medicine. Abstract and Presentation. ISE International Conference. May 4, 2010. 24 pages.

Panova et al., In situ fluorescence imaging of localized corrosion with a pH-sensitive imaging fiber. *Anal Chem.* Apr. 15, 1997; 69(8): 1635-41.

Pantano et al., Analytical applications of optical imaging fibers. *Anal Chem.* Aug. 1, 1995; 67(15):481A-487A.

Pantano et al., Ordered nanowell arrays. Chemistry of Materials. 1996;8: 2832-2835.

Pantano et al., Toward a near-field optical array. Rev. Sci. Instrum. 1997; 68(3): 1357-1359.

Peterson et al., Fiber optic pH probe for physiological use. *Anal Chem.* May 1980; 52(6):864-9.

Prabhakar et al., Simultaneous quantification of proinflammatory cytokines in human plasma using the LabMAP assay. J Immunol Methods. Feb. 1, 2002;260(1-2):207-18.

Qiu et al., Fluorescence single-molecule counting assays for high-sensitivity detection of cytokines and chemokines. *Clin Chem.* Nov. 2007; 53(11):2010-2.

Randle et al., Integrating molecular detection and response to create self-signalling antibodies. *Biochem Biophys Res Commun.* Nov. 12, 2004; 324(2):504-10.

Rissin et al., Attomolar detection of proteins in serum using single molecule enzyme-linked immunosorbent assays. Quanterix Corporation. Oak Ridge Conference, San Jose, CA. Poster. 2010. 1 page.

Rissin et al., Digital concentration readout of single enzyme molecules using femtoliter arrays and Poisson statistics. *Nano Lett.* Mar. 2006; 6(3):520-3.

Rissin et al., Digital readout of target binding with attomole detection limits via enzyme amplification in femtoliter arrays. *J Am Chem Soc.* May 17, 2006; 128(19):6286-7.

Rissin et al., Distinct and long-lived activity states of single enzyme molecules. J Am Chem Soc. Apr. 16, 2008; 130(15):5349-53. Epub Mar. 5, 2008.

Rissin et al., Duplexed sandwich immunoassays on a fiber-optic microarray. *Anal Chim Acta.* Mar. 30, 2006; 564(1):34-9. Epub Nov. 11, 2005.

Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.

Rissin et al., Simultaneous detection of single molecules and singulated ensembles of molecules enables immunoassays with broad dynamic range. Anal Chem. Mar. 15, 2011;83(6):2279-85. Epub Feb. 23, 2011.

Rissin et al., Single-molecule enzyme-linked immunosorbent assay detects serum proteins at subfemtomolar concentrations. *Nat Biotechnol.* Jun. 2010; 28(6):595-9 and supplemental pages. Epub May 23, 2010.

Roeffaers et al., Single-molecule fluorescence spectroscopy in (bio)catalysis. *Proc Natl Acad Sci U S A.* Jul. 31, 2007; 104(31):12603-9. Epub Jul. 30, 2007.

Rondelez et al., Highly coupled ATP synthesis by F1-ATPase single molecules. *Nature.* Feb. 17, 2005; 433(7027):773-7.

Rondelez et al., Microfabricated arrays of femtoliter chambers allow single molecule enzymology. Nat Biotechnol. Mar. 2005; 23(3):361-5. Epub Feb. 20, 2005.

Rotman, Measurement of activity of single molecules of beta-D-galactosidase. *Proc Natl Acad Sci U S A.* Dec. 15, 1961; 47:1981-91.

Schauer et al., A cross-reactive, class-selective enzymatic array assay. *J Am Chem Soc.* Sep. 26, 2001; 123(38):9443-4.

Schmidinger, et al., Inhibitor and protein microarrays for activity-based recognition of lipolytic enzymes. *Chembiochem.* Mar. 2006; 7(3):527-34.

Schweitzer et al., Inaugural article: immunoassays with rolling circle DNA amplification: a versatile platform for ultrasensitive antigen detection. *Proc Natl Acad Sci U S A.* Aug. 29, 2000; 97(18):10113-9.

Seydack, Nanoparticle labels in immunosensing using optical detection methods. *Biosens Bioelectron.* Jun. 15, 2005; 20(12):2454-69. Epub Dec. 16, 2004.

Shen et al. High-throughput SNP genotyping on universal bead arrays. Mutat Res. Jun. 3, 2005;573(1-2):70-82.

Shephard et al., Array-based binary analysis for bacterial typing. *Anal Chem.* Jan. 1, 2005; 77(1):319-26.

Song et al., Detecting biological warfare agents. *Emerg Infect Dis.* Oct. 2005; 11(10):1629-32.

Song et al., Fiber-optic microsphere-based arrays for multiplexed biological warfare agent detection. Anal Chem. Feb. 15, 2006; 78(4):1023-33.

(56) References Cited

OTHER PUBLICATIONS

Song et al., Single molecule measurements of tumor necrosis factor α andinterleukin-6 in the plasma of patients with Crohn's disease. J Immunol Methods Sep. 30, 2011;372(1-2):177-86. Epub Jul. 27, 2011.
Soukka et al., Supersensitive time-resolved immunofluorometric assay of free prostate-specific antigen with nanoparticle label technology. Clin Chem. 2001; 47(7):1269-78.
Stamou et al., Self-assembled microarrays of attoliter molecular vessels. *Angew Chem Int Ed Engl*. Nov. 24, 2003; 42(45):5580-3.
Steemers et al., Multi-analyte sensing: from site-selective deposition to randomly ordered addressable optical sensors. Microchimica Acta. 1999; 131:99-105.
Steemers et al., Screening unlabeled DNA targets with randomly ordered fiber-optic gene arrays. *Nat Biotechnol*. Jan. 2000; 18(1):91-4.
Stitzel et al., Array-to-array transfer of an artificial nose classifier. *Anal Chem*. Nov. 1, 2001; 73(21):5266-71. Epub Sep. 28, 2001.
Subbaraman, Detecting single cancer molecules. Technol Rev. Jun. 3, 2010. Last accessed at http://www.technologyreview.com/biomedicine/25462/ on Jan. 31, 2012. 2 page.
Sykes et al., Quantitation of targets for PCR by use of limiting dilution. Biotechniques. 1992;13(3):444-9.
Szunerits et al., "Aluminum Surface Corrosion and the Mechanism of Inhibitors Using pH and Metal Ion Selective Imaging Fiber Bundles," *Analytical Chemistry*, 2002, 74(4), 886-894.
Szunerits et al., "Fabrication of an Optoelectrochemical Microring Array," *Analytical Chemistry*, 2002, 74(7), 1718-1723.
Szunerits et al., Spatially resolved electrochemiluminescence on an array of electrode tips. *Anal Chem*. Sep. 1, 2003; 75(17):4382-8.
Szunerits et al., The use of optical fiber bundles combined with electrochemistry for chemical imaging. Chemphyschem. Feb. 17, 2003; 4(2):186-92. Epub Feb. 7, 2003.
Szurdoki et al., A duplexed microsphere-based fluorescent immunoassay. Anal Biochem. Apr. 15, 2001; 291(2):219-28.
Tam et al., An imaging fiber-based optical tweezer array for microparticle array assembly. Applied Physics Letters. 2004; 84(21):4289-4291.
Tam et al., Fabrication and optical characterization of imaging fiber-based nanoarrays. *Taianta*. Sep. 15, 2005;67(3):498-502. Epub Jul. 27, 2005.
Tam et al., Parallel microparticle manipulation using an imaging fiber bundle-based optical tweezer array and a digital micromirror device. Applied Physics Letters. 2006; 89:194101/1-194101/3.
Tan et al., Monitoring the reactions of single enzyme molecules and single metal ions. Anal. Chem. 1997; 69:4242-4248.
Taylor et al., Application of high-density optical microwell arrays in a live-cell biosensing system. Anal Biochem. Feb. 15, 2000; 278(2):132-42.
Tessler et al., Protein quantification in complex mixtures by solid phase single-molecule counting. Anal Chem. Sep. 1, 2009; 81(17):7141-8.
Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009.
Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/on Jan. 31, 2012. 4 pages.
Todd et al., Ultrasensitive flow-based immunoassays using single-molecule counting. Clin Chem. Nov. 2007; 53(11):1990-5. Epub Sep. 21, 2007.
Tromberg et al., Development of antibody-based fiber-optic sensors for detection of a benzo[a]pyrene metabolite. Anal Chem. Sep. 15, 1988; 60(18):1901-8.
Ueberfeld et al., Reversible ratiometric probe for quantitative DNA measurements. Anal Chem. Feb. 15, 2004; 76(4):947-52. Epub Jan. 20, 2004.
Vo-Dinh et al., Phase-resolved fiber-optics fluoroimmunosensor. Applied Spectroscopy. 1990;44(1):128-132.
Vogelstein et al., Digital PCR. Proc Natl Acad Sci U S A. Aug. 3, 1999;96(16):9236-41.
Walt et al., Biosensing with live cells using a high-density optical fiber array. Radiation Research. 2001; 156(4):442.
Walt et al., Microsensor arrays for saliva diagnostics. Ann N Y Acad Sci. Mar. 2007;1098:389-400.
Walt et al., Optical sensor arrays for odor recognition. Biosens Bioelectron. Sep. 15, 1998;13(6):697-9.
Walt et al., Ultrasensitive detection of proteins using single molecule arrays (SiMoA). Presented Mar. 1, 2010. Pittcon. Abstract and PowerPoint presentation. 32 pages.
Walt, An array of solutions, fiber arrays contribute to studies of individual cellular behavior and response. SPIE'S oemagazine. 2005; 19-21.
Walt, Fiber optic array biosensors. Biotechniques. Nov. 2006; 41(5):529, 531, 533, 535 passim.
Walt, Fiber optic imaging sensors. Accounts of Chemical Research. 1998; 31:267-278.
Walt, Imaging optical sensor arrays. *Curr Opin Chem Biol*. Oct. 2002; 6(5):689-95.
Walt, Techview: molecular biology. Bead-based fiber-optic arrays. *Science*. Jan. 21, 2000;287(5452):451-2.
Wang et al., Quantification of protein based on single-molecule counting by total internal reflection fluorescence microscopy with adsorption equilibrium. *Anal Chim Acta*. May 2, 2007; 590(1):104-9. Epub Mar. 15, 2007.
Warren et al., Transcription factor profiling in individual hematopoietic progenitors by digital RT-PCR. Proc Natl Acad Sci U S A. Nov. 21, 2006;103(47):17807-12. Epub Nov. 10, 2006.
Whitaker et al., Fiber-based single cell analysis of reporter gene expression in yeast two-hybrid systems. *Anal Biochem*. Jan. 1, 2007; 360(1):63-74. Epub Oct. 30, 2006.
Whitaker et al., Multianalyte single-cell analysis with multiple cell lines using a fiber-optic array. Anal Chem. Dec. 1, 2007; 79(23):9045-53. Epub Nov. 1, 2007.
White et al., An olfactory neuronal network for vapor recognition in an artificial nose. *Biol Cybern*. Apr. 1998; 78(4):245-51.
White et al., Rapid analyte recognition in a device based on optical sensors and the olfactory system. Analytical Chemistry. 1996; 68(13):2191-2202.
Wilson et al., Development of AccuPSA™, a novel digital immunoassay for sub-femtomolar measurement of PSA in post radical prostatectomy patients. AACR Molecular diagnostics in Cancer Therapeutic Development Abstract and Poster. 2011. 1 page.
Wilson et al., Fifth-generation digital immunoassay for prostate-specific antigen by single molecule array technology. Clin Chem. Dec. 2011;57(12):1712-21. Epub Oct. 13, 2011.
Wilson, Serum Measurement of Hypoxia-Induced Amyloid Beta 1-42 Following Resuscitation from Cardiac Arrest. Abstract and Poster. American Academy of Neurology Annual Meeting. Feb. 8, 2011. 2 pages.
Wu et al., Development and preliminary clinical validation of a high sensitivity assay for cardiac troponin using a capillary flow (single molecule) fluorescence detector. *Clin Chem*. Nov. 2006; 52(11):2157-9.
Xie et al., Optical studies of single molecules at room temperature. *Annu Rev Phys Chem*. 1998;49:441-80.
Xie et al., Single gold nanoparticles counter: an ultrasensitive detection platform for one-step homogeneous immunoassays and DNA hybridization assays. J Am Chem Soc. Sep. 9, 2009;131(35):12763-70.
Xue et al., Differences in the chemical reactivity of individual molecules of an enzyme. *Nature*. Feb. 23, 1995; 373(6516):681-3.
Young et al., Integrating high-content screening and ligand-target prediction to identify mechanism of action. Nat Chem Biol. Jan. 2008; 4(1):59-68. Epub Dec. 9, 2007.

* cited by examiner

METHODS AND ARRAYS FOR TARGET ANALYTE DETECTION AND DETERMINATION OF TARGET ANALYTE CONCENTRATION IN SOLUTION

RELATED APPLICATIONS

This application is a continuation of U.S. patent application Ser. No. 15/205,497, filed Jul. 8, 2016, which is a continuation of U.S. patent application Ser. No. 14/638,245, filed Mar. 4, 2015, and issued as U.S. Pat. No. 9,395,359 on Jul. 19, 2016, by Walt, et al., which is a continuation of U.S. patent application Ser. No. 13/870,596, filed Apr. 25, 2013, by Walt et al., now abandoned, each of which is incorporated herein by reference. U.S. patent application Ser. No. 13/870,596, filed Apr. 25, 2013, is a continuation of U.S. patent application Ser. No. 11/707,385, filed Feb. 16, 2007, and issued as U.S. Pat. No. 8,460,879 on Jun. 11, 2013, by Walt et. al., which claims priority under 35 U.S.C. § 119(e) to U.S. Provisional Patent Application Ser. No. 60/775,692, filed Feb. 21, 2006, by Rissin et al., and U.S. Provisional Patent Application Ser. No. 60/792,736, filed Apr. 17, 2006, by Rissin et al., each of which is incorporated herein by reference. U.S. patent application Ser. No. 13/870,596, filed Apr. 25, 2013, is also a continuation of U.S. patent application Ser. No. 11/707,383, filed Feb. 16, 2007, and issued as U.S. Pat. No. 8,460,878 on Jun. 11, 2013, by Walt et. al., which claims priority under 35 U.S.C. § 119(e) to U.S. Provisional Patent Application Ser. No. 60/775,692, filed Feb. 21, 2006, by Rissin et al., and U.S. Provisional Patent Application Ser. No. 60/792,736, filed Apr. 17, 2006, by Rissin et al., each of which is incorporated herein by reference. U.S. patent application Ser. No. 13/870,596, filed Apr. 25, 2013, is also a continuation of U.S. patent application Ser. No. 11/707,384, filed Feb. 16, 2007, and issued as U.S. Pat. No. 8,492,098 on Jul. 23, 2013, by Walt et. al., which claims priority under 35 U.S.C. § 119(e) to U.S. Provisional Patent Application Ser. No. 60/775,692, filed Feb. 21, 2006, by Rissin et al., and U.S. Provisional Patent Application Ser. No. 60/792,736, filed Apr. 17, 2006, by Rissin et al., each of which is incorporated herein by reference.

GOVERNMENT RIGHTS

The United States government may have certain rights in this invention pursuant to Contract No. N00014-01-1-0659 awarded by the Department of Defense, Defense Advanced Research Projects Agency (DARPA) Office of Naval Research.

BACKGROUND

Methods that implement high-sensitivity and low-level analyte detection in conjunction with rapid and reproducible experimental protocols are the cornerstone of modern analytical measurements. Currently, most known techniques for quantifying low levels of target analyte in a sample matrix use amplification procedures to increase the number of reporter molecules and thereby provide a measurable signal. These known processes include enzyme-linked immunosorbent assays (ELISA) for amplifying the signal in antibody-based assays, as well as the polymerase chain reaction (PCR) for amplifying target DNA strands in DNA-based assays. A more sensitive but indirect protein target amplification technique, called immuno-PCR (see Sano, T.; Smith, C. L.; Cantor, C. R. *Science* 1992, 258, 120-122), makes use of oligonucleotide markers, which can subsequently be amplified using PCR and detected using a DNA assay (see Nam, J. M.; Thaxton, C. S.; Mirkin, C. A. *Science* 2003, 301, 1884-1886; Niemeyer, C. M.; Adler, M.; Pignataro, B.; Lenhert, S.; Gao, S.; Chi, L. F.; Fuchs, H.; Blohm, D. *Nucleic Acids Research* 1999, 27, 4553-4561; and Zhou, H.; Fisher, R. J.; Papas, T. S. *Nucleic Acids Research* 1993, 21, 6038-6039). While the immuno-PCR method permits ultra low-level protein detection, it is a complex assay procedure, and can be prone to false-positive signal generation (see Niemeyer, C. M.; Adler, M.; Wacker, R. *Trends in Biotechnology* 2005, 23, 208-216).

One disadvantage of these known methods is their reliance on separate steps to amplify reporter molecules to provide a measurable signal, thereby requiring additional amplification steps and thus additional time, equipment, and materials.

In addition, known methods for accurately quantifying the concentration of a particular analyte in solution are all based on ensemble responses in which many analyte molecules give rise to the measured signal.

Therefore, there is a need in the art for an improved method and system of target analyte detection.

BRIEF SUMMARY OF THE INVENTION

According to one embodiment, the present invention relates to a method of detecting a target analyte in a sample. The method includes providing an array comprising a plurality of sites, each site comprising a capture component, and contacting the array with the sample such that each site in a subset of the plurality of sites contains a single target analyte. Each target analyte comprises an enzymatic component. The method further includes contacting the array with an enzymatic substrate and detecting a change in an optical property at each of the sites as an indication of the presence of the target analyte.

The present invention, in another embodiment, relates to a method of detecting target analytes in a sample. The method includes providing an array comprising a plurality of sites, and contacting the array with the sample such that each site in a first subset of the plurality of sites contains a single first target analyte and each site in a second subset of the plurality of sites contains a single second target analyte. In this embodiment, each site comprises a capture component and each of the first and second target analytes comprises an enzymatic component. The method further includes contacting the array with a first enzymatic substrate and detecting any change in an optical property as a result of the first enzymatic substrate at each of the sites as an indication of the presence of one of the first or second target analytes. In addition, the method includes washing the array and contacting the array with a second enzymatic substrate. Further, the method includes detecting any change in an optical property as a result of the second enzymatic substrate at each of the sites as an indication of the presence of one of the first or second target analytes.

In accordance with another embodiment, the present invention relates to a method of detecting a target analyte in a sample. The method includes providing an array comprising a plurality of sites and contacting the array with the sample such that each site in a subset of the plurality of sites contains a single target analyte. In this method, each site comprises a capture component. The method also includes contacting each of the single target analytes with a binding ligand comprising an enzymatic component and further contacting the array with an enzymatic substrate. In addition, the method includes detecting a change in an optical property at each of the sites as an indication of the presence of the target analyte.

The present invention, according to a further embodiment, is a method of quantifying an amount of a target analyte in a sample. The method includes providing an array comprising a plurality of sites, each site comprising a capture component and contacting the array with the sample such that each site in a subset of the plurality of sites contains a single target analyte. In this embodiment, each target analyte comprises an enzymatic component. The method also includes contacting the array with an enzymatic substrate, detecting a change in an optical property at each of the sites as an indication of the presence of the target analyte, and calculating an amount of the target analyte in the sample.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 7a is a microscopic photograph of a solution of $Ru(bpy)_3Cl_2$ enclosed in the array of chambers. FIG. 7b is a microscopic photograph of a small octagonal portion of the bundle photobleached with UV light. FIG. 7c is a microscopic photograph of FIG. 7b taken 60 minutes later.

FIG. 8a is a microscopic photograph of a background image of a portion of an array. FIG. 8b is a microscopic photograph of an image taken of a portion of a 1:5 enzyme to vessel assay. FIG. 8c is a microscopic photograph of a 1:80 enzyme to vessel assay.

DETAILED DESCRIPTION

Figures 1A, 1B, 1C, 1D:
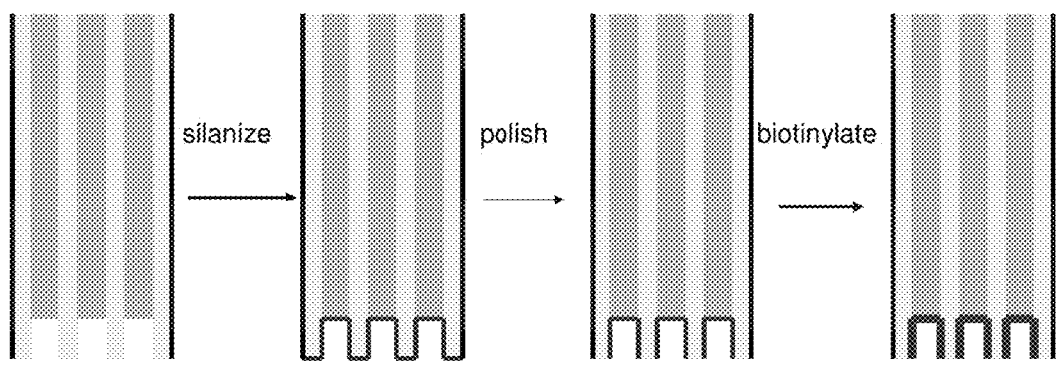
FIGS. 1a, 1b, 1c, and 1d are side view cross-section schematics representing etched bundle modifications, according to one embodiment of the present invention.

The present invention relates to methods, systems, and devices for enzymatic detection and quantification of a target analyte or target analytes in a sample. More specifically, the present invention relates to enzymatic detection and quantification of target analytes using arrays of micron- to nanoscale-sized reaction vessels containing capture components. According to one embodiment, an array of reaction vessels containing capture components is contacted with a sample containing at least one target analyte. A chromogenic substrate is then added and the resulting chromogenic product of the enzymatic reaction allows for detection of the analyte. Further, according to one embodiment, the percentage of reaction vessels with captured target analytes can be used to calculate the amount of target analyte in the sample using a binary readout method.

More specifically, the present invention provides for an array of micron- to nanoscale-sized reaction vessels specifically functionalized and capable of capturing target molecules that are enzymes or enzyme-labelled. The ability to immobilize the target allows the use of washing steps and indirect assays, as outlined below. In use, single enzyme (or enzyme-labelled) molecules are captured in individual reaction vessels and catalyze the production of a sufficient number of chromogenic product molecules to generate a detectable signal. In accordance with one embodiment relating to samples having low target analyte concentrations, only a portion of the reaction vessels bind a target molecule, thereby enabling a binary readout of target concentration from the array.

Thus, the direct enzymatic amplification in the method and system of the present invention allows for direct amplification of a detectable signal. Further, unlike the prior art methods, the present invention allows for detection of low concentrations of protein.

The quantification method, according to one embodiment, is a novel method for concentration determination based on statistical analysis. The sample enzyme concentration is determined by distributing the enzyme-containing sample and a suitable substrate, into many nanoscale reaction vessels. In this method, the vessels contain either zero or one enzyme molecule. By observing the presence or absence of a fluorescent product resulting from single enzyme molecule catalysis in each reaction vessel, a binary readout method can be used to count enzyme molecules. Finally, the percentage of reaction vessels occupied by enzyme molecules is correlated to the bulk enzyme concentration.

I. Arrays

The present invention provides array compositions comprising at least a first substrate with a surface comprising a plurality of assay locations. By "array" herein is meant a plurality of capture components in an array format. The size of the array will depend on the composition and end use of the array. Arrays containing from about 2 different capture components to many millions can be made, with very large arrays being possible, including very large fiber optic arrays. Generally, the array will comprise from two to as many as a billion or more capture components, depending on the size of the wells and the substrate, as well as the end use of the array, thus very high density, high density, moderate density, low density and very low density arrays may be made.

Preferred ranges for very high density arrays are from about 10,000,000 to about 2,000,000,000, with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 50,000 being particularly preferred, and from about 20,000 to about 30,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, multiple substrates may be used, either of different or identical compositions. Thus for example, large arrays may comprise a plurality of smaller substrates.

The compositions comprise a substrate. By "substrate", "array substrate" or "solid support" or other grammatical equivalents herein is meant any material that can be modified to contain discrete individual sites appropriate for the attachment or association of target analytes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, composite materials, ceramics, and plastic resins, silica or silica-based materials including silicon and modified silicon, carbon, metals, inorganic glasses, plastics, optical fiber bundles, and a variety of other polymers. In general, the substrates allow optical detection and do not appreciably fluoresce.

In one embodiment, the substrate comprises the end of an optical fiber bundle. Alternatively, the substrate does not comprise the ends of an optical fiber bundle. For example, the substrate may be a spotted, printed or photolithographic substrate known in the art; see for example WO 95/25116; WO 95/35505; PCT US98/09163; U.S. Pat. Nos. 5,700,637; 5,807,522 and 5,445,934; and U.S. Ser. Nos. 08/851,203 and 09/187,289, and references cited within, all of which are expressly incorporated by reference. One advantage of using the distal end of a optical fiber bundle as a substrate in the present invention is that the individual fibers in contact with each well can be used to carry both excitation and emission light to and from the wells, enabling remote interrogation of the well contents. Further, an array of optical fibers provides the capability for simultaneous excitation of molecules in adjacent vessels, without signal "cross-talk" between fibers. That is, excitation light transmitted in one fiber does not escape to a neighboring fiber.

In one embodiment, the substrate is planar, although as will be appreciated by those in the art, other configurations of substrates may be used as well; for example, three dimensional configurations can be used. Preferred substrates include optical fiber bundles as discussed below, and flat planar substrates such as glass, polystyrene and other plastics and acrylics.

In one embodiment, at least one surface of the substrate is modified to contain discrete, individual sites (also referred to herein as "reaction vessels" and "microwells") for later association of target analytes. These sites generally comprise physically altered sites, i.e. physical configurations such as wells or small depressions in the substrate that can retain the beads. The microwells may be formed as is generally known in the art using a variety of techniques, including, but not limited to, photolithography, stamping techniques, molding techniques and microetching techniques. As will be appreciated by those in the art, the technique used will depend on the composition and shape of the substrate.

In one embodiment, physical alterations are made in a surface of the substrate to produce the sites. In a preferred embodiment, the substrate is a fiber optic bundle and the surface of the substrate is a terminal end of the fiber bundle. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells. In one aspect of the present invention, the physical alterations can be made as taught in U.S. Pat. Nos. 6,023,540, 6,327,410, and 6,858,394, which are each incorporated by reference herein in their entirety.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate.

In accordance with one embodiment of the present invention, the reaction vessels have a volume ranging from about 10 attoliters to about 50 picoliters. Alternatively, the reaction vessels range in size from about 1 femtoliter to about 1 picoliter. In a further alternative, the reaction vessels range from about 30 femtoliters to about 60 femtoliters.

In one aspect of the present invention, the array is a fiber optic array. The array, according to one embodiment, can be made as follows. First, the reaction vessels are formed on the distal end of a fiber optic bundle. According to one embodiment, the vessels are created using an etching process, such as, for example, an acid etching process, resulting in reaction vessels of the desired volume. That is, the etching process creates depressions or holes in the core material at the end of the fiber bundle, while the cladding material is not impacted, thus resulting in reaction vessels. Alternatively, both the core material and cladding material are etched, but the cladding material is etched at a slower rate than the core material, thereby resulting in reaction vessels. One advantage of the fiber optic array format is that it circumvents a complicated microfabrication procedure and provides the ability to observe many reaction vessels simultaneously.

II. Capture Components

The microwells of the present invention comprise at least one capture component. A capture component (also referred to as a "capture binding ligand," "binding ligand," "capture binding species," or "capture probe") is any molecule, compound, or microwell modification that can be used to probe for, attach, bind or otherwise capture a target analyte within a microwell on the substrate, such that the target analyte is immobilized during the assay. Generally, the capture binding ligand or component allows the attachment of a target analyte to the microwell, for the purposes of detection, quantification, or other analysis.

As will be appreciated by those in the art, the composition of the capture component will depend on the composition of the target analyte. Capture components for a wide variety of analytes are known or can be readily found using known techniques. For example, when the analyte is a protein, the capture components or binding ligands include proteins (particularly including antibodies or fragments thereof (FAbs, etc.)) or small molecules. Preferred capture component proteins include peptides. For example, when the analyte is an enzyme, suitable binding ligands include substrates and inhibitors. Antigen-antibody pairs, receptor-ligands, and carbohydrates and their binding partners are also suitable analyte-binding ligand pairs. In addition, when the analyte is a single-stranded nucleic acid, the binding ligand may be a complementary nucleic acid. Similarly, the analyte may be a nucleic acid binding protein and the capture binding ligand is either single-stranded or double stranded nucleic acid; alternatively, the binding ligand may be a nucleic acid-binding protein when the analyte is a single or double-stranded nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptomers" can be developed for binding to virtually any target analyte. As will be appreciated by those in the art, any two molecules that will associate may be used, either as an analyte or as the capture component. Similarly, there is a wide body of literature relating to the development of capture components based on combinatorial chemistry methods.

Suitable analyte/capture component pairs include, but are not limited to, antibodies/antigens, receptors/ligands, proteins/nucleic acid, enzymes/substrates and/or inhibitors, carbohydrates (including glycoproteins and glycolipids)/lectins, proteins/proteins, proteins/small molecules; and carbohydrates and their binding partners are also suitable analyte-binding ligand pairs. These may be wild-type or derivative sequences. According to one embodiment, the capture components are portions (particularly the extracellular portions) of cell surface receptors that are known to multimerize, such as the growth hormone receptor, glucose transporters (particularly GLUT 4 receptor), transferring receptor, epidermal growth factor receptor, low density lipoprotein receptor, high density lipoprotein receptor, epidermal growth factor receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor, PDGF receptor, EPO receptor, TPO receptor, ciliary neurotrophic factor receptor, prolactin receptor, and T-cell receptors.

In a preferred embodiment, the capture component is attached to the microwell or reaction vessel as outlined herein, for example via an "attachment component" (also referred to herein as an "attachment linker"). An "attachment component," as used herein, is defined as any component, functionalization, or modification of the microwells that results in the attachment of the capture component, and can include bonds and/or linkers. Alternatively, the capture component may utilize a capture extender component. In this embodiment, the capture component or binding ligand comprises a first portion that will bind the target analyte and a second portion that can be used for attachment to the surface.

The method of attachment of the capture binding ligand to the attachment linker will generally be done as is known in the art, and will depend on the composition of the attachment linker and the capture binding ligand. In general, the capture binding ligands are attached to the attachment linker through the use of functional groups on each that can then be used for attachment. According to one embodiment, the functional group is a chemical functionality. That is, the microwell surface is derivatized such that a chemical functionality is bound to the surface. Preferred functional groups for attachment are amino groups, carboxy groups, oxo groups and thiol groups. These functional groups can then be attached, either directly or through the use of a linker, sometimes referred to herein as a "cross-linker." Linkers are known in the art; for example, homo- or hetero-bifunctional linkers as are well known (see 1994 Pierce Chemical. Company catalog, technical section on cross-linkers, pages 155-200, incorporated herein by reference). Preferred linkers include, but are not limited to, alkyl groups (including substituted alkyl groups and alkyl groups containing heteroatom moieties), with short alkyl groups, esters, amide, amine, epoxy groups and ethylene glycol and derivatives being preferred. Linkers may also be a sulfone group, forming sulfonamide.

According to one embodiment, the functional group is a light-activated functional group. That is, the functional group can be activated by light to attach to the target analyte or to the crosslinker. One example is the PhotoLink™ technology available from SurModics, Inc. in Eden Prairie, Minn.

In one alternative aspect of the invention, the functional group is added without derivatizing the well surface. That is, the functional groups can be added to the surface by adding a molecule having an attached functional group attached, wherein the molecule has a binding affinity for the well surface. The molecule, according to one embodiment is bovine serum albumin. Alternatively, the molecule is any protein capable of binding or sticking to the vessel surface. In a further alternative, the molecule is any molecule capable of binding or sticking to the vessel surface. In one example, the molecule is bovine serum albumin with free amine groups on its surface. The crosslinker can then be added to attach to the amine groups.

According to one exemplary embodiment in which the capture component is a chemical crosslinker, the target analyte is attached using chemical crosslinking in the following manner. First, the reaction vessel surface is derivatized with a functional group such as $NH_2$. Next, the crosslinker and the target analyte are added to the array such that the crosslinker attaches to the $NH_2$ and the target analyte attaches to the crosslinker. In an alternative embodiment described in further detail below in which the target analyte is not an enzyme, a label having an enzymatic component can also be attached to the target analyte.

In this way, capture binding ligands comprising proteins, lectins, nucleic acids, small organic molecules, carbohydrates, etc. can be added.

One embodiment utilizes proteinaceous capture components or capture binding ligands. As is known in the art, any number of techniques may be used to attach a proteinaceous capture binding ligand. "Protein" in this context includes proteins, polypeptides, peptides, including, for example, enzymes. A wide variety of techniques are known to add moieties to proteins. One preferred method is outlined in U.S. Pat. No. 5,620,850, hereby incorporated by reference in its entirety. The attachment of proteins to surfaces is known; see also Heller, Acc. Chem. Res. 23:128 (1990), and related work.

An alternative embodiment utilizes nucleic acids as the capture binding ligand, for example for when the target analyte is a nucleic acid or a nucleic acid binding protein, or when the nucleic acid serves as an aptamer for binding a protein, as is well known in the art.

According to one embodiment, each microwell comprises a plurality of capture components. The plurality of capture components, in one aspect of the invention, are distributed on the surface of the well like a "lawn." Alternatively, the capture components are distributed in any known fashion.

The binding between the capture component and the target analyte, in accordance with one embodiment, is specific and the capture component is part of a binding pair. That is, the capture component is a target specific capture component that specifically binds with or has specificity for the target analyte. More specifically, the capture component binds specifically and directly to the target analyte. By "specifically bind" or "binding specificity" herein is meant that the capture component binds the analyte with specificity sufficient to differentiate between the analyte and other components or contaminants of the test sample. For example, the capture component according to one embodiment is an antibody that binds specifically to some portion of the target analyte. The antibody, according to one embodiment, can be any antibody capable of binding specifically to a target analyte. For example, appropriate antibodies include, but are not limited to, monoclonal antibodies, bispecific antibodies, minibodies, domain antibodies, synthetic antibodies (sometimes referred to as "antibody mimetics"), chimeric antibodies, humanized antibodies, antibody fusions (sometimes referred to as "antibody conjugates"), and fragments of each, respectively.

However, as will be appreciated by those in the art, it is possible to detect analytes using binding which is not highly specific; for example, the systems may use different capture components such as, for example, an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding. In some embodiments, for example in the detection of certain biomolecules, the binding constants of the analyte to the binding ligand will be at least about $10^4$-$10^6$ M$^{-1}$, with at least about $10^5$ to $10^9$ M$^{-1}$ being preferred and at least about $10^7$-$10^9$ M$^{-1}$ being particularly preferred.

According to one embodiment in which the target analyte is a cell, including, for example, bacterial cells, the capture component is an adhesin receptor molecule. In use, the adhesin receptor molecule binds with a surface protein called an adhesin on the extracellular surface of the target cell, thereby immobilizing or capturing the cell. Alternatively, in embodiments in which the target analyte is another type of cell (a non-bacterial cell), the capture component is an appropriate cell surface receptor that binds the target analyte cell. In a further embodiment in which the target analyte is a cell, the capture component is fibronectin. For example, fibronectin can be used when the target analyte is a nerve cell.

Alternatively, the capture component is a non-specific capture component. That is, the capture component does not bind specifically to a target analyte, but rather binds to a corresponding binding partner associated with or attached to the target analyte. For example, the non-specific capture component according to one embodiment is a chemical cross-linker as described above. According to one embodiment, every peptide molecule in a target sample can attach to the chemical cross-linker. This type of system can be used to identify enzyme target analytes because the analytes are detected by modifying the substrate.

In one example of a non-specific capture component according to one embodiment, the capture component is streptavidin, which binds with high affinity to biotin, and thus binds to any molecule to which biotin has been attached. Alternatively, the capture component is biotin, and streptavidin is attached to or associated with the target analyte such that the target analyte can be captured by the biotin.

According to one embodiment, the capture component is added to the reaction vessels in the following manner. First, the microwells are prepared for attachment of the capture component(s). That is, the microwells are modified or an attachment component is added to the microwells such that the capture component(s) will attach to the microwells. In one embodiment, the microwells are derivatized with a chemical functionality as described above. Next, the capture component is added.

One example of capture component attachment is depicted in FIG. 1, in which reaction vessels of the present invention are functionalized with biotin. As shown in FIG. 1a, the array of the present invention in this example is a fiber optic bundle 10. To attach the capture component 18, the microwells are first modified with an attachment component 16, which in this example is an aminopropyl silane 16 that is bound to both the core 12 and cladding 14 surfaces of the distal end of the fiber bundle 10, as shown in FIG. 1b. The modification with aminopropyl silane is effective in this example because NHS-biotin attaches to an amino-silanized surface 16. However, since the capture component 18 should be present only within the reaction vessels, the external surfaces of the substrate, such as the external surfaces of the cladding 14, should not be silanized. That is, the silanization must be removed from the external cladding surface 14 to avoid biotin attachment. In this example as shown in FIG. 1c, the silanization 16 was removed from the external cladding layer 14 by polishing the amino-silanized fibers for 10 seconds with 0.3 μm lapping film, thereby removing the top amino-silanized cladding layer.

After the attachment component 16 has been added to the microwells, the capture component 18 can be attached. In the example in FIG. 1, the capture component 18 is biotin 18. As shown in FIG. 1d, biotin succinimidyl ester 18 is attached to the amino groups 16 on the well surfaces 12.

III. Target Analytes

As discussed herein, the array of the present invention provides for detection, quantification, and further analysis of target analytes. By "target analyte" or "analyte" or grammatical equivalents herein is meant any atom, molecule, ion, molecular ion, compound or particle to be either detected or evaluated for binding partners.

According to one embodiment, the target analyte is an enzyme. For example, the enzyme can be an enzyme from any of the six enzyme classifications: oxidoreductases, transferases, hydrolases, lyases, isomerases, and ligases. Thus, appropriate enzymes include, but are not limited to, polymerases, cathepsins, calpains, amino-transferases such as, for example, AST and ALT, proteases such as, for example, caspases, nucleotide cyclases, transferases, lipases, enzymes associated with heart attacks, and the like. When the system of the present invention is used to detect viral or bacterial targets, appropriate enzymes include viral or bacterial polymerases and other such enzymes, including viral or bacterial proteases.

Alternatively, the target analyte has an enzymatic component. For example, the target analyte can be a cell having an enzyme or enzymatic component present on its extracellular surface. Alternatively, the target analyte is a cell having no enzymatic component. Such a cell is typically identified using an indirect assaying method described below such as a "sandwich" assay.

In accordance with another embodiment, the target analyte is not an enzyme. As will be appreciated by those in the art, a large number of analytes may be used in the present invention; basically, any target analyte can be used which binds a capture component and/or a secondary binding ligand. As will be explained in further detail below, these target analytes are typically identified using an indirect assay such as a "sandwich" assay. As mentioned above, one suitable target analyte is a cell. In addition, suitable analytes include organic and inorganic molecules, including biomolecules. In a preferred embodiment, the target analyte is a protein. As will be appreciated by those in the art, there are a large number of possible proteinaceous target analytes that may be detected or evaluated for binding partners using the present invention. In addition to enzymes as discussed above, suitable protein target analytes include, but are not limited to, (1) immunoglobulins; (2) hormones and cytokines (many of which serve as ligands for cellular receptors); and (3) other proteins.

According to one embodiment in which the target analyte is not an enzyme and a sandwich assay is performed as described in further detail below, the enzymatic label as described in further detail below can be beta galactosidase. Alternatively, the enzyme label can be, but is not limited to, alkaline phosphatase or horseradish peroxidase.

Further suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc.

IV. Enzymatic Substrate

After the target analyte(s) are captured within the microwell(s) (and after a washing step, according to certain embodiments), a reaction component is added to the array. By "reaction component," as used herein, is meant a molecule that affects an enzymatic reaction when contacted with an enzyme or enzymatic molecule. By "affects" a reaction is meant to include, but is not limited to, inducing, activating, or altering (for example, slowing down or speeding up) a reaction, or inhibiting a reaction. According to one embodiment, the reaction component is a chromogenic enzymatic substrate. A "chromogenic enzymatic substrate" as used herein is any molecule that is converted by an enzyme into a chromogenic product as a result of an enzymatic reaction. "Chromogenic" means relating to color or pigment in the optical (visible light) spectrum and includes fluorogenic.

It is understood in the art that chromogenic substrates are known or can be made for enzymes in any of the six enzyme classifications. Thus, any known chromogenic substrate capable of producing a chromogenic product in a reaction with a particular enzyme can be used in the present invention, including any of the chromogenic enzyme substrates disclosed in *The Handbook—A Guide to Fluorescent Probes and Labeling Technologies*, Tenth Ed., Chapter 10, http://probes.invitrogen.com/handbook/sections/1000.html, which is incorporated herein by reference in its entirety.

According to one embodiment in which the assay of the present invention is a sandwich assay as described further herein in which the enzyme label is beta galactosidase, the substrate added to the array is a beta galactosidase substrate such as resorufin-β-D-galactopyranoside.

V. Assay Methods

The array of the present invention can be used for several different assay methods. More specifically, the present invention provides for both (a) target analyte detection and (b) quantification of target analyte concentration in a sample.

Generally, the system or array of the present invention is exposed to an analyte of interest (or contacted with a sample containing an analyte of interest) and the analyte is immobilized by a capture component in a microwell, under conditions suitable for immobilization of the target analyte to at least one of the capture components, i.e. generally physiological conditions. For purposes of the present application, the term "immobilized" means attached, bound, or affixed to a capture component in a microwell. Thus, the interaction between any analyte molecule and the capture component in a microwell results in immobilization of the analyte molecule within that microwell.

According to one aspect of the invention, the sample of interest is placed in contact with the array of the present invention (or the array is incubated in the sample) for a period of from about 45 minutes to about 75 minutes. Alternatively, the array and sample are contacted for a period of from about 50 minutes to about 70 minutes. In a further alternative, the incubation period is about 1 hour.

According to one embodiment, a wash step is performed after contacting the array with the sample. The wash step is intended to wash away any target analytes or non-target molecules that are not bound to a capture component. Alternatively, no wash step is needed.

In one aspect of the invention, a secondary binding ligand is then added to the array. Generally, the secondary binding ligand is added if the assay is an indirect assay such as a "sandwich assay" (when the target analyte is not an enzyme), as described in further detail herein. The secondary binding ligand, as discussed above, will associate with or bind to the bound target analyte and comprises an enzymatic component. The secondary binding ligand is added in an amount sufficient to ensure that a ligand comes into contact with every bound target analyte in the array. Alternatively, no secondary binding ligand is added, such as, for example, when the target analyte is going to be detected directly.

A chromogenic enzymatic substrate as described above is then introduced or added to the array. The chromogenic enzymatic substrate is provided in an amount sufficient to contact any captured target analyte. The chosen substrate reacts with or is modified by the enzymatic component such that the reaction produces a chromogenic product and thus an optical signal. The presence of the chromogenic product in the array can provide information about the identity and/or concentration of an analyte based on the interaction of the analyte with the capture component and the enzymatic substrate (and the secondary binding ligand, in some cases).

In one embodiment of the present invention, the microwells are sealed after the enzymatic substrate is added. That is, a sealing component is placed in contact with the face of the substrate, thereby fluidly isolating each microwell and sealing its contents therein. A "sealing component," as used herein, is defined as any material or device large enough to cover the entire surface of the array substrate and capable of contacting the array substrate surface such that each reaction vessel is sealed or isolated such that the contents of each vessel cannot escape the vessel. According to one embodiment, the sealing component is a silicone elastomer gasket that is placed against the substrate surface with a uniform pressure across the entire substrate. By sealing the contents in each microwell, the enzymatic reaction can proceed within the microwell, thereby producing a detectable amount of the chromogenic product that is retained in the microwell for detection purposes. That is, the enzyme converts the substrate into a chromogenic product that builds up to a locally high concentration in each sealed vessel, generating a detectable chromogenic signal.

According to one embodiment, the present invention provides for a microscope system equipped with a mechanical platform that applies the sealing component. The platform is positioned beneath the microscope stage on the microscopy system. After the assay contents have been added to each well, the sealing component is sandwiched between a flat surface (such as, for example, a microscope slide) and the array substrate using uniform pressure applied by the mechanical platform.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

The microwells exhibiting activity or changes in their optical signature may be identified by a conventional optical train and optical detection system. Depending on the particular chromogenic enzymatic substrates used and the operative wavelengths of their chromogenic products, optical filters designed for a particular wavelengths may be employed for optical interrogation of the microwells. In a preferred embodiment, the system or array of the present invention is used in conjunction with an optical fiber bundle or fiber optic array as a substrate.

According to one embodiment, the array of the present invention can be used in conjunction with an optical detection system such as the system described in U.S. application Ser. No. 09/816,651, which is incorporated herein by reference in its entirety. For example, according to one embodiment, the array of the present invention is the distal end of a fiber optic assembly comprising a fiber optic bundle constructed of clad fibers so that light does not mix between fibers. As depicted in the Ser. No. 09/816,651 Applications, the proximal end of the bundle is received by a z-translation stage and x-y micropositioner.

The optical detection system of U.S. application Ser. No. 09/816,651 operates as follows. Light returning from the distal end of the bundle is passed by the attachment to a magnification changer which enables adjustment of the image size of the fiber's proximal or distal end. Light passing through the magnification changer is then shuttered and filtered by a second wheel. The light is then imaged on a charge coupled device (CCD) camera. A computer executes imaging processing software to process the information from the CCD camera and also possibly control the first and second shutter and filter wheels.

The array or system of the present invention may be attached to the distal end of the optical fiber bundle using a variety of compatible processes. Wells are formed at the center of each optical fiber of the bundle. Thus, each optical fiber of the bundle conveys light from the single microwell formed at the center of the fiber's distal end. This feature is necessary to enable the interrogation of the optical signature of individual microwells to identify reactions in each microwell. Consequently, by imaging the end of the bundle onto the CCD array, the optical signatures of the microwells are individually interrogatable.

A. Detection

In one aspect of the present invention, the present array can be used to detect the presence of a target analyte in a sample. More specifically, the invention provides a method for detecting the product of the enzymatic reaction as an indication of the presence of the target analyte.

The method of detection can proceed either directly or indirectly. If the target analyte is an enzyme, the analyte can be identified by a direct method of detection. Alternatively, if the target analyte is not an enzyme and thus cannot produce a chromogenic product in the presence of a chromogenic enzymatic substrate, the analyte is identified by an indirect method of detection.

The direct method of detection, which involves a target analyte that is an enzyme, proceeds as follows. First, the sample of interest and the array are placed in contact as described in further detail above under suitable conditions. Subsequently, the chromogenic enzymatic substrate is added.

The presence or absence of the target analyte in any given microwell is then detected by optical interrogation. That is, any change in the optical signal caused by production of a chromogenic product is detected. In any microwell containing the target analyte, the analyte modifies or acts upon the substrate in some way, thereby resulting in the release of a chromogenic product, resulting in a change in the optical signal from the microwell. The chromogenic reaction product is then optically detected.

In one embodiment of the present invention, the microwells are sealed after the enzymatic substrate is added, as described above.

The indirect methods of detection involve a target analyte that does not have enzymatic properties. Two indirect methods that can be used with the present invention are the "sandwich" assay and the "competitive" assay.

Figure 2A:
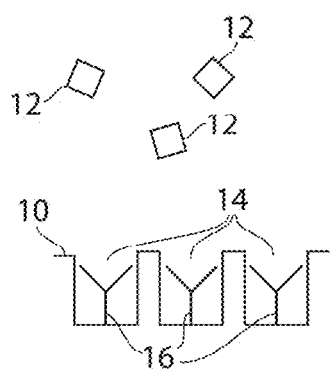
FIGS. 2a, 2b, and 2c are side view cross-section schematics representing a sandwich assay, according to one embodiment of the present invention.
Figure 2B:
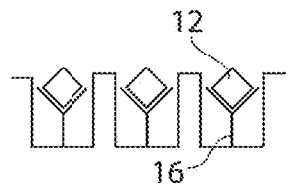

A sandwich assay can be performed as depicted in FIG. 2. First, the sample of interest and the array 10 are placed in contact as shown in FIG. 2a and as described in further detail above. Under suitable conditions, target analyte 12 present in the sample is captured by the capture components 16 in the microwells 14, as shown in FIG. 2b. According to one embodiment, a wash step is then performed.

Figure 2C:
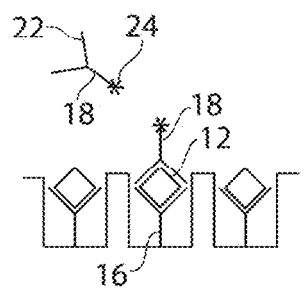

Next, a solution binding ligand 18 (also referred to herein as a "secondary binding ligand") is added to the array 10, as shown in FIG. 2c. Solution binding ligands 18 are similar to capture components 16 in that they bind to target analytes 12. The solution binding ligand 18 may be the same or different from the capture binding ligand 16. The binding of the solution binding ligand 18 to a captured target analyte 12 forms a "sandwich" of sorts. In the absence of the target analyte, the solution binding ligand 18 is washed away.

A solution binding ligand 18 has two components—a binding component 22 and an enzymatic label 24. The binding component 22 is the portion of the solution binding ligand 18 that binds to the target analyte 12. Typically, the solution binding ligand 18 binds to a different portion of the target analyte 12 than the capture component 16, because if both the capture component 16 and solution binding ligand 18 were to bind to the same portion, the solution binding ligand 18 would not be capable of binding to a captured target analyte 12. Thus, the chosen secondary binding ligand 18 can bind to the target analyte 12 while the target analyte 12 is bound to a microwell 14 via a capture component 16.

The enzymatic label 24 is the portion of the solution binding ligand 18 that exhibits enzymatic activity. According to one embodiment, the enzymatic label 24 is an enzyme attached to the solution binding ligand 18.

Subsequently, the chromogenic enzymatic substrate is added.

In one embodiment of the present invention, the microwells are sealed after the enzymatic substrate is added, as described above.

The presence or absence of the target analyte in any given microwell is then detected by optical interrogation. That is, any change in the optical signal caused by production of a chromogenic product is detected. In any microwell containing the target analyte and the secondary binding ligand, the enzyme associated with the secondary binding ligand modifies or acts upon the substrate in some way, thereby producing a chromogenic product, resulting in a change in the optical signal from the microwell. The product is then optically detected.

The competitive assay operates as follows. First, a labelled molecule is added to the array of the present invention, wherein the label is a enzyme or enzymatic component. In this embodiment, the chosen labelled molecule binds with the capture component such that the addition of the labelled molecule to the array results in labelled molecules being bound to capture components in the microwells.

Next, the sample of interest and the array are placed in contact as described in further detail above. The presence of the target analyte in the array causes the displacement of the labelled molecule and binding of the analyte to the capture components. The displacement occurs for the following reason: in this embodiment, the chosen capture component is capable of binding to either of the labelled molecule or the target analyte, thus resulting in a competitive binding situation. As a result, if a labelled molecule is bound to a capture component in a microwell and a target analyte is added, the target analyte will displace the labelled molecule under suitable conditions.

According to one embodiment, a wash step is then performed to remove any non-bound labelled molecules from the array.

Subsequently, the chromogenic enzymatic substrate is added. And as discussed above, according to one aspect of the invention, the microwells are sealed after the enzymatic substrate is added. Alternatively, the microwells are not sealed.

The presence or absence of the target analyte in any given microwell is then detected by optical interrogation. But unlike the optical interrogations that are described above, in this interrogation it is the lack of a chromogenic product that indicates the presence of the target analyte in the microwell. In any microwell containing the target analyte, no enzymatic action occurs and no change occurs in the optical signal from the microwell. In contrast, in any microwell in which the labelled molecule is still present, an optical signal is detected.

In an alternative version of the competitive assay embodiment, both the labelled molecule and sample of interest are added to the array at the same time in fixed volumes. In this version, the target analyte and labelled molecule compete directly for the binding sites on the capture components.

1. Subpopulations of Identical Capture Components to Same Target Analyte

In accordance with one detection embodiment, sensor redundancy is used. In this embodiment, a plurality of reaction vessels comprising identical capture components referred to as "subpopulations" are used. That is, each subpopulation comprises a plurality of identical capture components present in microwells of the array. Further, according to one embodiment, each subpopulation comprises a plurality of microwells comprising identical capture components. By using a number of identical capture components for a given array, the optical signal from each microwell can be combined for the subpopulation and any number of statistical analyses run, as outlined below. This can be done for a variety of reasons. For example, in time varying measurements, redundancy can significantly reduce the noise in the system. For non-time based measurements, redundancy can significantly increase the confidence of the data.

The number of subpopulations, according to one embodiment, can range from 2 to any number of subpopulations possible given the limitations of any known array and the number of different capture components. Alternatively, the number can range from about 2 to about 10. In a further alternative, the number can range from about 2 to about 5.

In one embodiment, a plurality of identical capture components are used. As will be appreciated by those in the art, the number of identical capture components in a subpopulation will vary with the application and use of the sensor array. In general, anywhere from 2 to thousands of identical capture components may be used in a given subpopulation, with from 2 to 100 being preferred, 2 to 50 being particularly preferred and from 5 to 20 being especially preferred. In general, preliminary results indicate that roughly 10 identical capture components in a subpopulation gives a sufficient advantage, although for some applications, more identical capture components can be used.

Once obtained, the optical response signals from a plurality of microwells within each subpopulation (that is, having the same capture component) can be manipulated and analyzed in a wide variety of ways, including baseline adjustment, averaging, standard deviation analysis, distribution and cluster analysis, confidence interval analysis, mean testing, etc.

2. Multiple Different Capture Components to Same Target Analyte

In addition to the sensor redundancy, the array of the present invention according to one embodiment utilizes a plurality of capture components that are directed to a single target analyte but are not identical. This embodiment provides for more than one different capture component in each microwell or different capture components in different microwells. In one example, a single target analyte may be provided to which two or more capture components are capable of binding. This adds a level of confidence as non-specific binding interactions can be statistically minimized. In this embodiment, when proteinaceous target analytes are to be evaluated, preferred embodiments utilize capture components that bind to different parts of the target. For example, when two or more antibodies (or antibody fragments) to different portions of the same target protein are used as capture components, preferred embodiments utilize antibodies to different epitopes. Similarly, when nucleic acid target analytes are to be evaluated, the redundant nucleic acid probes may be overlapping, adjacent, or spatially separated. However, it is preferred that two probes do not compete for a single binding site, so adjacent or separated probes are preferred.

In this embodiment, a plurality of different capture components may be used, with from about 2 to about 20 being preferred, and from about 2 to about 10 being especially preferred, and from 2 to about 5 being particularly preferred, including 2, 3, 4 or 5. However, as above, more may also be used, depending on the application.

3. Multiple Different Capture Components to Multiple Target Analytes

According to another embodiment, the array of the present invention utilizes a plurality of different capture components that are directed to a plurality of target analytes. This embodiment includes more than one different capture component in each microwell or different capture components in different microwells. In one example, two or more target analytes may be provided to which two or more capture components in the same microwells or different microwells are capable of binding.

In this embodiment, more than one target analyte can be identified. For example, two or more target analytes can be identified so long as each different analyte is a different enzyme or has a different enzymatic component such as a enzymatic surface molecule. In one embodiment, the target analytes are identified using multiple enzymatic substrates wherein each substrate produces a different color upon interaction with the appropriate enzyme. Thus, each target analyte can be distinguished based on the color produced by reaction with the substrate. In an alternative embodiment, the target analytes are identified using multiple substrates that each produce the same color. Thus, each target analyte can be distinguished by added the substrates sequentially.

In this embodiment, a plurality of different capture components may be used, with from about 2 to about 20 being preferred, and from about 2 to about 10 being especially preferred, and from 2 to about 5 being particularly preferred, including 2, 3, 4 or 5. However, as above, more may also be used, depending on the application.

Please note that each of the different assay configurations above, including the capture component subpopulations directed to different target analytes and the plurality of capture components directed to the same analyte, can also be utilized for quantification as described below.

B. Quantification

According to one embodiment of the present invention, the present array cannot only be used for detection of a target analyte in a sample, but also for quantification of the analyte in the sample. That is, there is a correlation between the percentage of reaction vessels containing target analytes and the concentration of the analyte in the sample. Thus, the quantification method of the present invention allows for calculation of the amount of a target analyte in a sample based on the percentage of microwells that captured a target analyte.

Without being limited by theory, the quantification method is driven in part by the fact that the number and volume of reaction vessels employed govern the dynamic range of concentrations that can be determined by this technique. That is, based on the number and volume of the reaction vessels in an array of the present invention, an estimate can be made of the range of concentrations of target analyte in solution that allow for the concentration to be determined using the method of the present invention.

For example, for an array as disclosed in Example 2 with reaction vessels each having a volume of 46 fL, a solution having a concentration of $3.6 \times 10^{-11}$ M β-galactosidase will yield, on average, one enzyme molecule per vessel. However, it is important to note that distributing a solution having a target analyte concentration within the appropriate range into an array of reaction vessels will not result in the distribution of exactly one enzyme molecule per vessel; statistically, some vessels will have multiple molecules while others will have zero. In the case where the number of enzyme molecules per vessel is high, the data can be fit to a Gaussian distribution. As the ratio of enzyme molecules to reaction vessels approaches zero, the Poisson distribution applies. This limiting distribution is used to calculate the probability of rare events occurring in a large number of trials. For example, based on Poisson statistics, for a concentration of $3.6 \times 10^{-11}$ M, a distribution between zero and five enzyme molecules per container is observed, with the most probable values being zero and one.

Equation 1 can be used to determine the probability of observing v events based on the expected average number of events per trial, μ.

$$P_\mu(v) = e^{-\mu}(\mu^v/v!) \qquad \text{Equation 1:}$$

If the concentrations used are much less than $3.6 \times 10^{-11}$ M, the expected average becomes exceptionally low, the distribution is narrowed, and the probability of observing anything other than 0 or 1 events per trial is improbable in all experimental cases. At these low concentrations, the relationship between the percentage of active reaction vessels and the bulk enzyme concentration is approximately linear. Thus, based on this knowledge, the array of the present invention can be used to determine the concentration of a target analyte in a sample by a simple digital readout system as described herein.

According to one embodiment, the quantification method of the present invention can be performed as follows. The method is a digital readout system (also referred to as a "binary readout system") that includes first detecting the target analytes in the array of microwells by any detection method described above. The number of reaction vessels is then counted and a percentage of the total number of reaction vessels is calculated. That is, utilization of a yes or no response, in conjunction with the high-density array of reaction vessels, permits the digital readout of bulk concentrations of β-galactosidase. This readout is accomplished by counting the vessels containing an active enzyme molecule across the array, with the resulting "active well" percentage correlating to the enzyme concentration. Given the large number of vessels simultaneously interrogated in the array of the present invention, the ratio of enzyme molecules to reaction vessels could be as low as 1:500, as the large number of wells provides a statistically significant signal even at this low ratio.

Without being limited by theory, it is believed that the quantification method of the present invention is only limited by the number of individual reaction vessels that can be viewed with an acceptable resolution. Thus, expanding the number of vessels that are interrogated by using higher density CCD chips will decrease the limit of detection as the lower limit is defined by the statistics of the small number of active wells that light up at the lower target concentrations. On the other hand, the upper limit of the dynamic range is controlled by the well-to-well deviation from a binary readout. As target concentrations are increased, the binary readout is lost, as a Gaussian distribution becomes a better approximation of target molecule binding. Higher concentrations of target lead to a broad distribution in the number of enzyme molecules that can occupy each well, and consequently, the transition to a non-linear increase in the percentage of active wells.

The limitations of this technique are realized above and below the thresholds of the dynamic range. As the concentration goes below the lower limit of the dynamic range, the number of enzyme molecules is too low to observe sufficient occupied wells and, therefore, the number of wells must be increased in order to make sure that a statistically significant number of them are occupied by enzyme molecules. Results for extremely dilute concentrations have large relative errors associated with them, due to the very small number of reaction vessels that are expected to show activity. Slight deviation from the expected Poisson value, in this case, will result in a large error. The ultimate upper limit to this technique occurs when 100% of the reaction vessels contain at least one enzyme molecule. At this limit, discrimination between two solutions of high enzyme concentrations is not feasible. As the percentage of active vessels approaches 100%, the linearity between concentration and active vessel percentage is lost. This situation results in a broadening distribution, as a normal distribution becomes an increasingly better approximation of the results.

In one aspect of the present invention, the array can also be used to analyze enzyme kinetics. "Enzyme kinetics" as used herein refers to the study of the rates of enzyme-controlled reactions. It is understood in the art of enzyme kinetics that the rate of an enzymatic reaction at low substrate concentrations is proportional to the substrate concentration (is "substrate dependent"). This is referred to as first order. It is further understood that the rate of the reaction at high substrate concentrations reaches a maximum rate and is independent of substrate concentration because the reaction becomes saturated. Thus, if reaction velocity is plotted as a function of substrate concentration, the line initially increases linearly with an increase in substrate and then begins to level off as substrate concentration approaches saturation.

Thus, according to one embodiment, the kinetics of any particular enzyme can be studied using the present system and array. Reaction velocity varies across enzymes for various reasons, including, for example, reaction inhibition caused by allosteric inhibition. The array of the present invention allows for study of these varied kinetic characteristics.

According to one embodiment, kinetics are examined in the following fashion. The target analyte is allowed to bind to the capture component, the substrate is added, and the reaction vessel is sealed. Given that a finite amount of substrate is present in the reaction vessel and that no further substrate can be added due to the sealing of the vessel, the reaction velocity can be determined based on the amount of chromogenic product detected over time.

VI. Exemplary Uses of the Present Invention

The system and array of the present invention has many uses. For example, the array has application to fundamental enzymology studies, as well as digital concentration measurements. Further, the array permits studies with multiple different enzymes and extends the limits of ultra-low detection for protein and DNA targets. With the ability to simultaneously monitor a large array of reaction vessels, single molecule enzymology can be used to resolve individual enzyme molecule behavior from bulk kinetic signal.

Another use, for example, is environmental monitoring of bacteria or viruses or both. An environmental sample potentially containing certain bacteria can be placed in contact with an array of the present invention. To detect the bacteria, the bacteria cells are lysed and a bacterial enzyme (or more than one enzyme) is targeted for detection. According to one embodiment, the cells are lysed prior to being added to the array. Alternatively, the cells are captured and a lysing step occurs on the array prior to detection. In a further alternative, no lysis may be necessary if a cell surface marker is targeted. For example, the bacteria or virus of interest can be captured with an antibody that is specific to a surface marker on the target, and then the capture can be detected with a sandwich-type assay by adding an enzyme-labelled antibody that binds to the target in another location.

Please note that all references disclosed herein are incorporated herein by reference in their entirety.

Although the present invention has been described herein with reference to preferred embodiments, persons skilled in the art will recognize that changes may be made in form and detail without departing from the spirit and scope of the invention.

EXAMPLES

Example 1

In this example, a proof-of-concept binding assay is performed using enzymatic signal amplification in an array of femtoliter sized reaction vessels. More specifically, various assays are performed to detect varying amounts of streptavidin-$\beta$-galactosidase (S$\beta$G) in solution using a biotinylated array of the present invention and then the correlation between the number of wells with captured S$\beta$G molecules and the concentration of the S$\beta$G in the sample is examined.

In this example, an etched fiber optic array is used to create a collection of femtoliter sized reaction vessels, each specifically functionalized and capable of capturing enzyme-labeled target molecules. Single enzyme molecules are confined to individual reaction vessels and catalyze the production of a sufficient number of fluorescent product molecules to generate a positive signal. At low target molecule concentrations, only a percentage of the capture sites bind a target molecule, enabling a binary readout of target concentration from the high-density array.

Materials

The reactor vessel arrays in this example are generated using an acid etch of the distal face of a polished 1 mm fiber optic array, consisting of 24,000 individual 4.5 µm optical fibers. The core fiber material is silica, and the cladding around each fiber is germania-doped silica, which etches at a slower rate. The 4.5 µm fibers are etched to a depth of 2.9 µm, creating an array of reactor vessels, each with a 46 fL volume (see FIG. 1a).

The fibers were first modified with an aminopropyl silane bound to both the core and cladding surfaces (see FIG. 1b). To avoid biotin attachment to the cladding, the amino-silanized fibers were polished for 10 seconds with 0.3 µm lapping film, which removed the top amino-silanized cladding layer from the fiber array (see FIG. 1c). After polishing, NHS-biotin was attached to the amino groups on the well surfaces (see FIG. 1d).

Methods

Figure 3A:
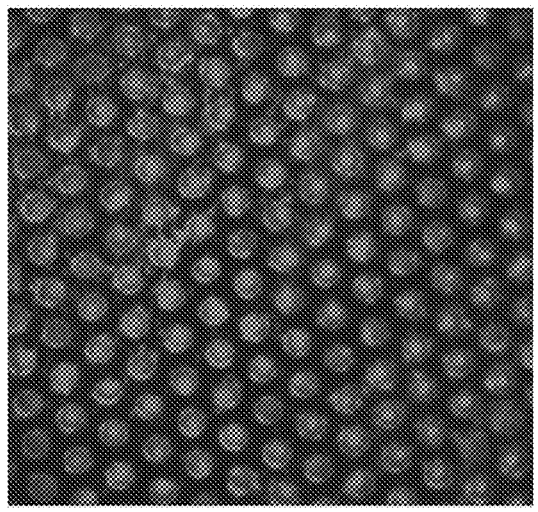
FIGS. 3a and 3b are photographs depicting Streptavidin Alexa Fluor 568® binding to (a) an unpolished biotin modified fiber optic array, and (b) a polished biotin modified fiber optic array, according to one embodiment of the present invention.
Figure 3B:
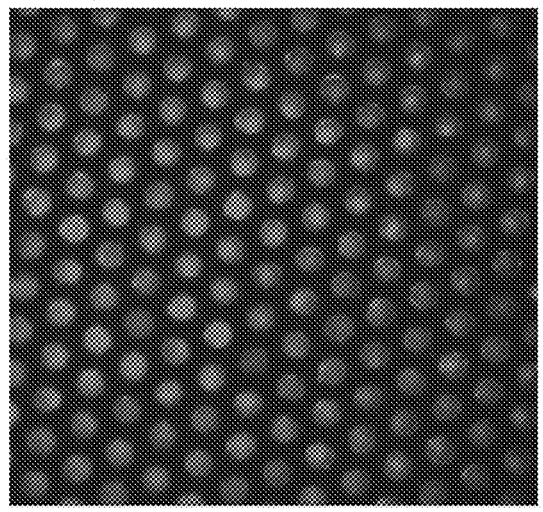
Figure 4A:
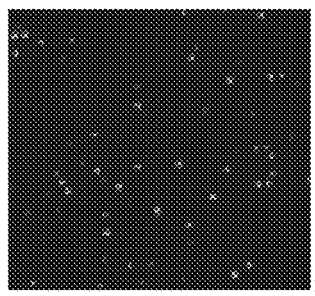
FIGS. 4a, 4b, 4c, 4d, 4e, and 4f are photographs depicting experiments according to one embodiment of the present invention in which β-galactosidase hydrolyzes RDG to form resorufin. More specifically, each of these figures depicts a different sample having a different concentration of SβG. The concentrations were: (a) 128 amol, (b) 51 amol, (c) 25 amol, (d) 7.5 amol, and (e) 2.6 amol, and (f) was the control.
Figure 4B:
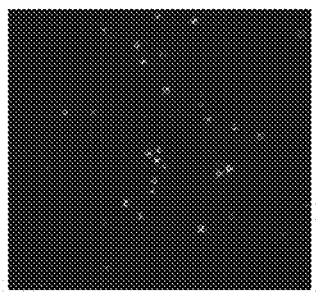
Figure 4C:
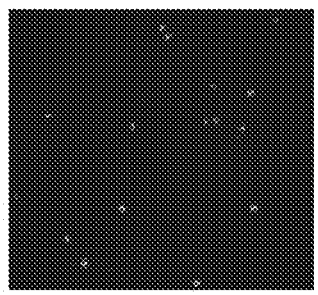
Figure 4D:
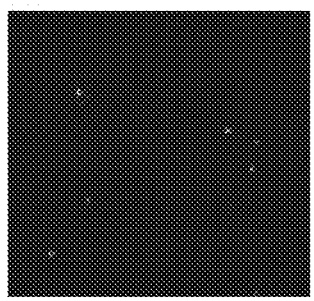
Figure 4E:
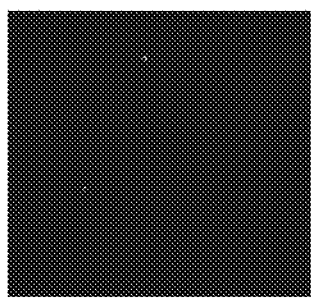
Figure 4F:
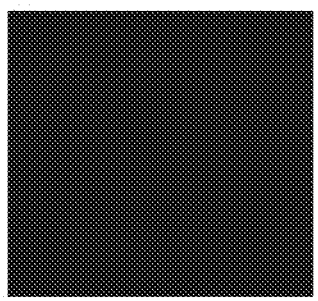

First, the effectiveness of the capture component was tested. To test the effectiveness of the biotinylation of the substrate, streptavidin Alexa Fluor 568® was attached directly to the biotin groups on the surfaces of both a polished and an unpolished fiber, followed by image acquisition of the modified surface (see FIG. 3). FIG. 3 shows Streptavidin Alexa Fluor 568® binding to (a) an unpolished biotin modified fiber optic array, and (b) a polished biotin modified fiber optic array. As seen in image (a), streptavidin binding occurred on all surfaces, in comparison to image (b), where binding occurred only on the surfaces of the microwell reactors. Thus, the unpolished fiber shows dye over the entire array including the cladding surface, while the polished fiber shows dye localized only on the well surfaces.

Subsequent to array modification, the biotinylated fiber arrays were incubated for 1 hour at room temperature in 150 µL PBS buffer containing varying amounts of S$\beta$G. The concentration of the S$\beta$G was chosen so that during the incubation time, statistically either one molecule or no molecules would bind to each well. The arrays were then washed repeatedly in PBS buffer, to ensure that unbound target was removed.

For a binary readout of SβG binding, the fiber array was loaded and secured on an upright microscope system equipped with a mechanical platform. A solution of β-galactosidase substrate, resorufin-6-D-galactopyranoside (RDG), was introduced to the distal end of the fiber containing the reaction vessels, and subsequently sealed. The substrate was sealed using a 0.01-inch thick silicone elastomer gasket sandwiched between a microscope slide and the fiber array by means of a mechanical platform located beneath the microscope stage. This platform applied a uniform pressure to the gasket material, across the entire bundle, sealing off each reaction chamber and enabling well to well interrogation of enzyme activity. β-galactosidase hydrolyzes RDG to form resorufin, which builds up to a locally high concentration in each sealed reaction vessel, generating a detectable fluorescent signal (FIG. 4).

FIG. 4 depicts a portion of the fiber array for each experiment. Each of the experiments tested a different sample having a different concentration of SβG. The concentrations for each experiment were as follows: (a) 128 amol, (b) 51 amol, (c) 25 amol, (d) 7.5 amol, and (e) 2.6 amol. FIG. 4(f) depicts the control.

Analysis of over 5000 reaction vessels for each experiment allowed for a correlation between the percentage of reaction vessels that captured an enzyme molecule and the amount of enzyme present in the interrogated sample. The variation seen in the intensity differences from active well to active well is most likely a result of molecule-to-molecule variation in catalytic activity, in combination with surface effects, which may modulate the relative activities of enzyme molecules based on their orientation to the reaction chamber surface.

Two control experiments were also conducted to ensure that the binding of enzyme to the surface of the reactors was based exclusively on the biotin-streptavidin interaction, and not on non-specific binding to the glass surface. One control experiment consisted of an etched, unmodified fiber incubated with the most concentrated SβG target solution (128 amol in 150 µL). The second control experiment was performed using the modified fiber incubated in a solution of β-galactosidase lacking streptavidin (128 amol in 150 µL). Both control experiments generated a negligible active well percentage (less than 0.06%, versus 0.2% for the 2.6 amol experiment discussed below).

Results

Figure 5:
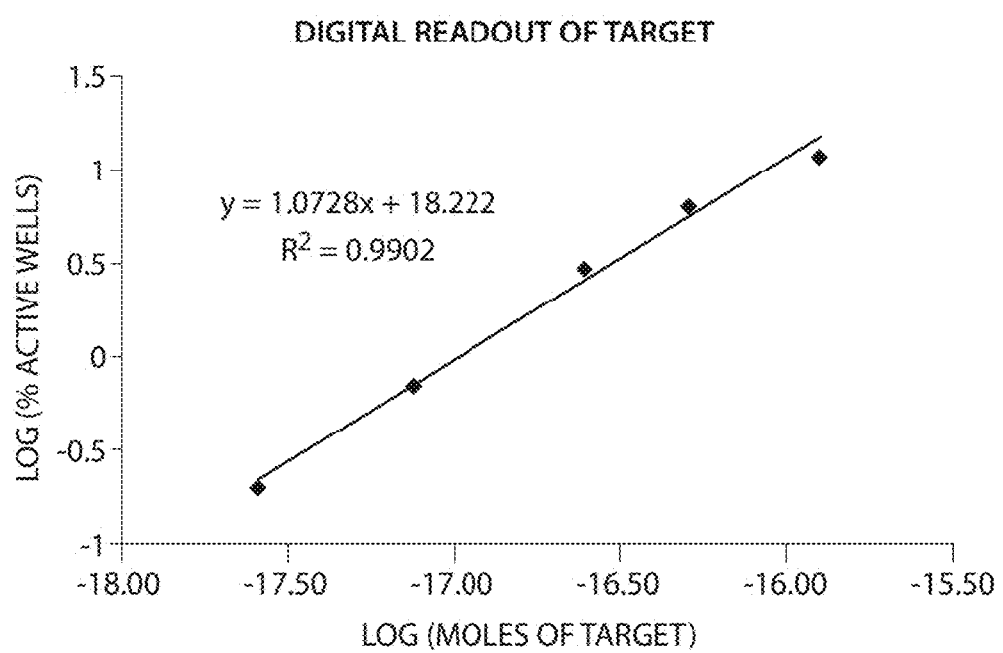
FIG. 5 is a chart depicting a log-log plt of the moles of target present in a sample with the resulting percentage of active reaction vessels, according to one embodiment of the present invention.

FIG. 5 depicts a log-log plot of the moles of target present in a sample with the resulting percentage of active reaction vessels. The linear relationship between the percentage of active reaction vessels and the moles of target in the log-log plot shown in FIG. 5 suggests that a binary readout detection method can be used for the detection of real targets such as DNA and antigens. This method permits rapid analysis and accurate concentration information via digital readout, while maintaining a straightforward assay procedure.

It is also interesting to note that the lowest limit of detection (LOD) for binding streptavidin-β-galactosidase (SβG) to a biotinylated femtoliter array in this example was 2.6 amoles (150 µL of 17 fM solution) using a target incubation time of 1 hour.

Example 2

In this example, single molecules of β-galactosidase were monitored using a 1 mm diameter fiber optic bundle with over $2.0 \times 10^5$ individually sealed, femtoliter microwell reactors. By observing the buildup of fluorescent products from single enzyme molecule catalysis over the array of reaction vessels and by applying a Poisson statistical analysis, a digital concentration readout was obtained.

Materials 1 mm bundled 4.5 µm optical fibers were purchased from Illumina (San Diego, Calif.). β-galactosidase and Ru(bpy)$_3$Cl$_2$ was obtained from Sigma-Aldrich (St. Louis, Mo.). Resorufin-D-β-galactopyranoside was purchased from Molecular Probes (Eugene, Oreg.). 0.01-inch non-reinforced gloss silicone sheeting material was purchased from Specialty Manufacturing Inc. (Saginaw, Mich.). All other chemicals used were of reagent grade and obtained from Sigma-Aldrich (St. Louis, Mo.).

A custom-built, upright epifluorescence imaging system acquired all fluorescence images using a mercury light source, excitation and emission filter wheels, microscope objectives, and a CCD camera (QE, Sensicam). Filter wheels and shutters were computer controlled and analysis was performed with IPlab software (Scanalytics, Fairfax, Va.). The system was equipped with a fastening device to fix the fiber optic array onto the system through the entire experiment. A mechanical platform beneath the stage was used to house the silicone-sealing layer, which was subsequently brought into contact with the distal end of the fiber array, sealing off each reaction vessel. All measurements were performed with femtowell arrays at the distal end of the optical fiber bundle.

Figure 6A:
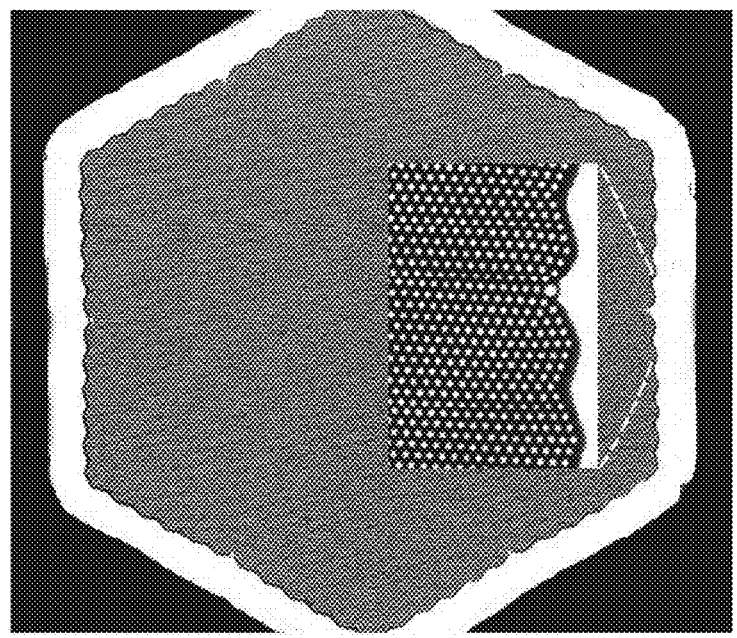
FIG. 6a is a microscopic photograph of an entire fiber array and an inset close-up of the bundle, according to one embodiment of the present invention.
Figure 6B:
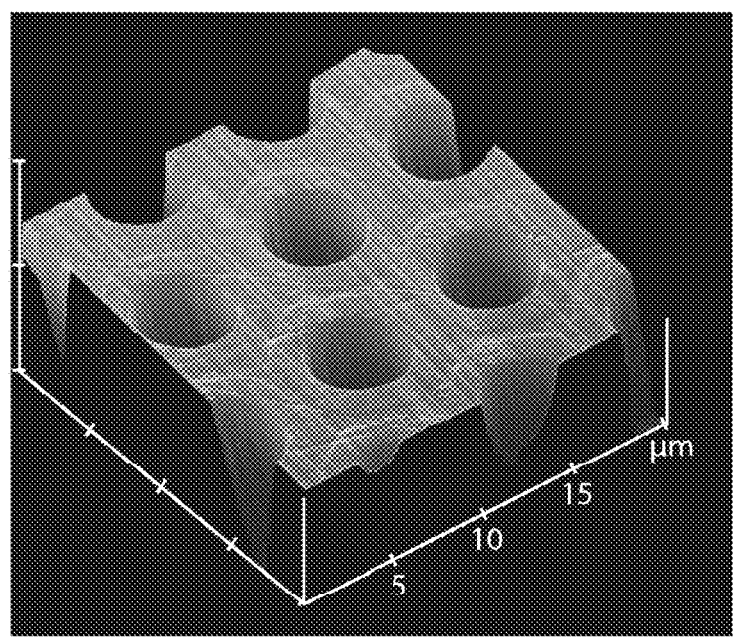
FIG. 6b is an AFM image of a portion of an etched surface, according to one embodiment of the present invention.

Optical fiber bundles containing approximately $2.4 \times 10^5$ individual 4.5 µm diameter optical fibers were used as the substrate for fabricating femtoliter reaction vessel arrays. The well volume can be precisely controlled, as etch depth varies with etch time and etchant concentration. The optical fibers used in these experiments were etched to a depth of approximately 2.9 µm, yielding a 46 fL well volume. FIG. 6 depicts images of the etched surface of the fiber optic bundles. More specifically, FIG. 6a depicts the entire fiber array and close-up microscope images of the fiber bundle, emphasizing the regularity of both the array and each individual optical fiber. Further, FIG. 6b is an AFM image of a portion of the etched surface, showing wells created from the etching process.

Methods

Assay.

For the β-galactosidase assay, the substrate used was resorufin-β-D-galactopyranoside. After the individual wells in the array were sealed in the presence of enzyme and substrate, the fluorescence intensity was monitored across the array of vessels for the enzymatic product, resorufin (ex 558 nm/em 573 nm). A 100 µM solution of resorufin-D-β-galactopyranoside (RDG) was prepared in 100 mM Tris buffer pH 8.0 containing 2.0 mM KCl and 0.1 mM MgCl$_2$. All enzyme solutions were prepared from previously aliquoted and frozen stock samples in the same reaction buffer. Just prior to experimentation, the two samples were centrifuged for 2 min at 7000 RPM to remove any particulate material that could interfere with the mechanics of the silicone seal. Approximately 1 cm$^2$ of silicone and a microscope slide were cleaned with absolute ethanol. The silicone sheeting was placed on the surface of the glass, to which it adhered. Subsequently, 75 µL volumes of enzyme and RDG solutions were mixed on the silicone gasket using a pipette. The gasket was mechanically raised towards the distal end of the fiber bundle until it experienced resistance, suggesting that a seal was formed. An initial fluorescence image was acquired, followed by periodic image acquisition for approximately 2 hr.

Sealing Component.

To seal the femtoliter array, a 0.01-inch thick silicone elastomer gasket was sandwiched between a microscope slide and the fiber array using a mechanical platform. This platform applied uniform pressure to the gasket material, across the entire bundle, sealing off each microwell to create the reaction vessels.

Figure 7A:
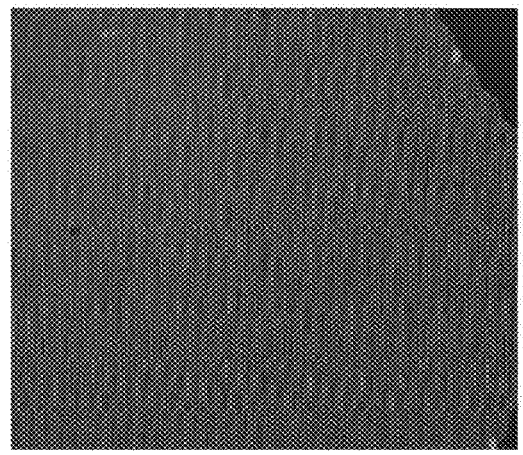
FIGS. 7a, 7b, and 7c depict enclosure of the reaction vessels and evaluation of the seal, according to one embodiment.
Figure 7B:
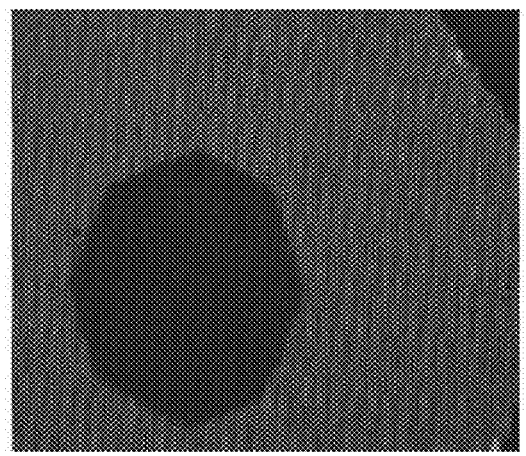
Figure 7C:
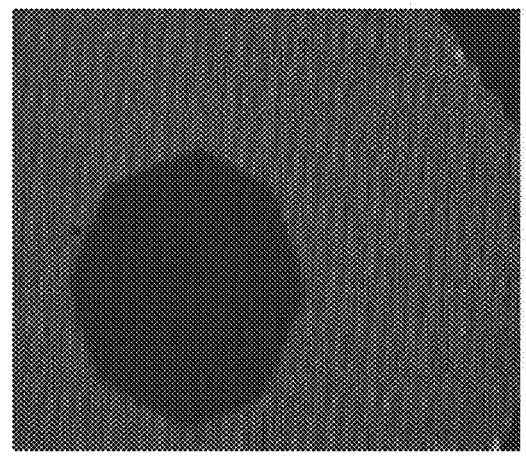

The silicone/glass seal used to create and isolate the femtoliter containers was inspected for its sealing ability by performing a photobleaching experiment (see FIG. 7). FIG. 7 depicts enclosure of a solution into the microchambers and evaluation of the silicone seal for integrity. FIG. 7a depicts a solution of $Ru(bpy)_3Cl_2$ enclosed into the array of chambers as observed by the red fluorescence across the array. FIG. 7b depicts a small octagonal portion of the fiber bundle that was photobleached via UV light. FIG. 7c depicts the array 60 minutes later. As shown in the figure, diffusion of $Ru(bpy)_3Cl_2$ from one well to another as a result of an imperfect silicone seal would display increased fluorescence intensity in photobleached wells and was not observed. This experiment substantiated the integrity of the seal for its ability to successfully isolate the array of vessels. Enzyme molecule denaturation on the glass surface was prevented by blocking with a BSA blocking buffer. Enzyme to vessel ratios used ranged from 1:5, down to 1:500, achieving accurate detection over two orders of magnitude.

Photobleaching Experiment.

A solution of 1 mM $Ru(bpy)_3Cl_2$ in DI water was used for the photobleaching experiments. A piece of silicone, approximately 1 $cm^2$, and a microscope slide were cleaned with absolute ethanol using lint-free swabs. The silicone sheeting was placed on the surface of the glass, to which it adhered. 50 μL of the $Ru(bpy)_3Cl_2$ solution was placed on the silicone, and subsequently brought into contact with the fiber bundle, to enclose the solution in the individual vessels. Using a field stop on the imaging system, UV light was used to illuminate a small portion of the array for 10 minutes, photobleaching the $Ru(bpy)_3Cl_2$. The field stop was then opened, and an image was acquired, displaying the difference in fluorescence. The array was then allowed to rest with the seal maintained. A final image was taken after 60 minutes, confirming the integrity of the seal.

As discussed above, the number and volume of reaction vessels employed govern the dynamic range of concentrations that can be determined by this technique. The reaction vessel volumes employed in this example were 46 fL (vide infra); therefore, it was calculated that a solution of $3.6 \times 10^{-11}$ M β-galactosidase will yield, on average, one enzyme molecule per vessel. As also discussed above, if the concentrations used are much less than $3.6 \times 10^{-11}$ M, the expected average becomes exceptionally low, the distribution is narrowed, and the probability of observing anything other than 0 or 1 events per trial is improbable in all experimental cases. At these low concentrations, the relationship between the percentage of active reaction vessels and the bulk enzyme concentration is approximately linear. After waiting for sufficient time to allow enzyme catalysis to occur, individual vessels were interrogated for an on/off response, correlating to each vessel either possessing or lacking enzymatic activity.

The substrate resorufin-D-β-galactopyranoside (RDG) was used as the substrate for experiments, which was sealed into all the vessels, along with the trapped enzyme molecules, using a silicone gasket material and mechanical arm. The expected percentages of active wells were calculated for each concentration used by applying the Poisson distribution statistics.

Results

Figure 8A:
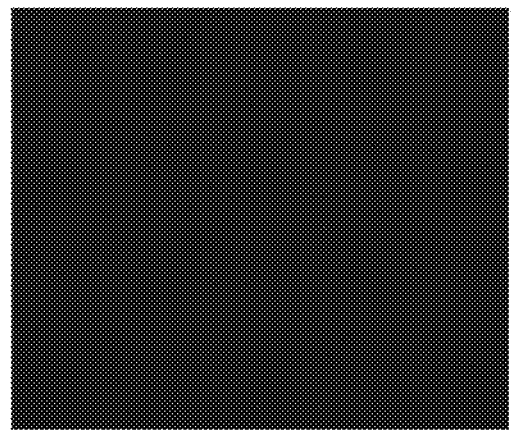
FIGS. 8a, 8b, and 8c are microscopic photographs depicting detection of the activity of single molecules of β-galactosidase, according to various embodiments of the present invention.
Figure 8B:
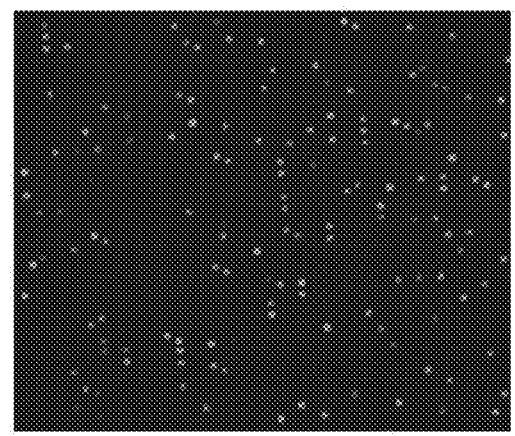
Figure 8C:
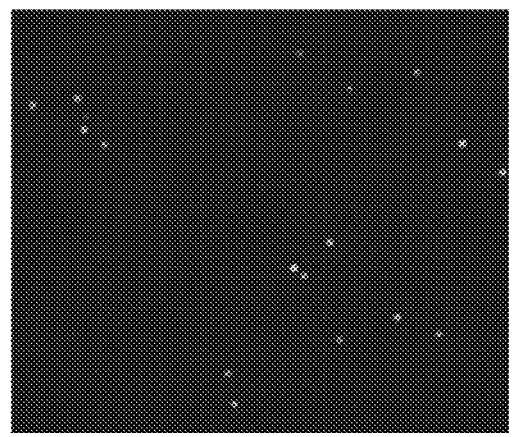

As shown in FIG. 8, for the β-galactosidase assay, different bulk solution enzyme concentrations correspond to different ratios of enzyme to vessel volume, resulting in variation in the percentage of vessels that contain an enzyme molecule. FIG. 8 depicts the detection of the activity of single molecules of β-galactosidase. FIG. 8a is a background image of a portion of the array, while FIG. 8b depicts an image taken of a portion of a 1:5 enzyme to vessel assay, and FIG. 8c shows a 1:80 enzyme to vessel assay.

Table 1 is a comparison of each experimental result with the percentage of occupied vessels calculated from the Poisson distribution. As shown by the data in the table, the array measurements successfully correlated with the number of single enzyme β-galactosidase molecules over the entire range of interrogated concentrations. There is minor disparity in the observed signals as a result of molecule-to-molecule variation in catalytic activity. This result is most likely due to the inherent stochastic nature of enzymes, in addition to surface effects, resulting in modulation of enzyme activity.

Digital Readout of Enzyme Concentrations

TABLE 1

Digital readout from the arrays. The actual percentage of chambers exhibiting activity, in comparison to the expected percentage calculated from the Poisson distribution, are listed for the various concentrations analyzed.

| Enzyme to well ratio | Concentration | Poisson % of active wells | Actual % active |
| --- | --- | --- | --- |
| 1:5 | 7.20E−12 | 18.2 | 14.9 |
| 1:10 | 3.60E−12 | 9.5 | 11.5 |
| 1:20 | 1.80E−12 | 4.9 | 5.6 |
| 1:40 | 9.00E−13 | 2.5 | 3.5 |
| 1:80 | 4.50E−13 | 1.2 | 1.5 |
| 1:100 | 3.60E−13 | 1.0 | 1.1 |
| 1:200 | 1.80E−13 | 0.5 | 0.3 |
| 1:500 | 7.20E−14 | 0.2 | 0.1 |

The variation between the calculated and experimental results can be attributed to the intrinsic variability associated with the probability distribution, as well as experimental error in the preparation of enzyme solutions.

BIBLIOGRAPHY

Each of the following references is incorporated by reference in their entirety.

Sano, T.; Smith, C. L.; Cantor, C. R. *Science* 1992, 258, 120-122.

Nam, J. M.; Thaxton, C. S.; Mirkin, C. A. *Science* 2003, 301, 1884-1886.

Niemeyer, C. M.; Adler, M.; Pignataro, B.; Lenhert, S.; Gao, S.; Chi, L. F.; Fuchs, H.; Blohm, D. *Nucleic Acids Research* 1999, 27, 4553-4561.

Zhou, H.; Fisher, R. J.; Papas, T. S. *Nucleic Acids Research* 1993, 21, 6038-6039.

Niemeyer, C. M.; Adler, M.; Wacker, R. *Trends in Biotechnology* 2005, 23, 208-216.

Whitesides, G. M. *Nature Biotechnology* 2003, 21, 1161-1165.

Rondelez, Y.; Tresset, G.; Tabata, K. V.; Arata, H.; Fujita, H.; Takeuchi, S.; Noji, H. *Nature Biotechnology* 2005, 23, 361-365.

Nakano, M.; Komatsu, J.; Matsuura, S.; Takashima, K.; Katsura, S.; Mizuno, A. *Journal of Biotechnology* 2003, 102, 117-124.

Nagai, H.; Murakami, Y.; Yokoyama, K.; Tamiya, E. *Biosensors and Bioelectronics* 2001, 16, 1015-1019.

Lipman, A. E.; Shuler, B.; Bakajin, O.; Eaton, W. A. *Science* 2003, 301, 1233-1235.

Chiu, D. T.; Wilson, C. F.; Ryttsen, F.; Stromberg, A.; Farre, C.; Karlsson, A.; Nordholm, S.; Gaggar, A.; Modi, B. P.; Moscho, A.; Garza-Lopez, R. A.; Orwar, O.; Zare, R. N. *Science* 1999, 283, 1892-1895.

Rissin, D. M.; Walt, D. R. *Journal of the American Chemical Society* submitted.

Pantano, P.; Walt, D. R. *Chemistry of Materials* 1996, 8, 2832-2835.

Monk, D. J.; Ueberfeld, J.; Walt, D. R. *Journal of Materials Chemistry* 2005, 15, 4361-4366.

Song, L. N.; Ahn, S.; Walt, D. R. *Emerging Infectious Diseases* 2005, 11, 1629-1632.

Lee, J. Y.; Li, H. W.; Yeung, E. S. *Journal of Chromatography A* 2004, 1053, 173-179.

Xue, Q. F.; Yeung, E. S. *Nature* 1995, 373, 681-683.

Foquet, M.; Korlach, J.; Zipfel, W. R.; Webb, W. W.; Craighead, H. G. *Analytical Chemistry* 2004, 76, 1618-1626.

Gratzl, M.; Lu, H.; Matsimoto, T.; Yi, C.; Bright, G. R. *Analytical Chemistry* 1999, 71, 2751-2756.

Stamou, D.; Duschl, C.; Delamarche, E.; Vogel, H. *Angewandte Chemie-International Edition* 2003, 42, 5580-5583.

Gosalia, D. N.; Diamond, S. L. Proceedings of the National Academy of Sciences USA 2003, 100, 8721-8726.

Lu, H. P.; Xun, L. Y.; Xie, X. S. *Science* 1998, 282, 1877-1882.

Taylor, J. R. *An Introduction to Error Analysis*; Second Addition ed.; University Science Books: Sausalito, C A, 1997.

Wheeler, A. R.; Throndset, W. R.; Whelan, R. J.; Leach, A. M.; Zare, R. N.; Liao, Y. H.; Farrell, K.; Manger, I. D.; Daridon, A. *Analytical Chemistry* 2003, 75, 3581-3586.

The invention claimed is:

1. A method of measuring the concentration of a target analyte in a sample using a competitive assay, comprising:
contacting labelled molecules and target analyte from the sample with a plurality of capture components capable of binding to the labelled molecule or the target analyte, wherein the target analyte competes with the labelled molecules for binding to the capture components, and wherein a captured labelled molecule generates an optical signal and a captured target analyte does not generate an optical signal;
immobilizing the plurality of capture components with respect to a plurality of reaction vessels comprising the capture components, wherein a portion of the plurality of reaction vessels contains capture components with immobilized labelled molecules, and another portion of the plurality of reaction vessels contains capture components that are not immobilized to labelled molecules;
determining a total percentage of the reaction vessels that do not contain a captured labelled molecule; and
determining the concentration of the target analyte in the sample from the total percentage.

2. The method of claim 1, wherein the plurality of reaction vessels comprise the capture components prior to the step of contacting the labelled molecules and the target analyte from the sample with the plurality of capture components.

3. The method of claim 1, further comprising removing any non-bound labelled molecules from the plurality of reaction vessels prior to the step of determining a total percentage of the reaction vessels that do not contain a captured labelled molecule.

4. The method of claim 3, further comprising determining a total percentage of the reaction vessels that contain target analyte from the total percentage of the reaction vessels that do not contain a captured labelled molecule.

5. The method of claim 3, wherein the step of determining a total percentage of the reaction vessels that do not contain a labelled molecule comprises determining the percentage of reaction vessels in which the optical signal is not generated.

6. The method of claim 3, wherein each capture component is capable of forming a binding complex in which it is bound to a single molecule that is either a labelled molecule or a target analyte.

7. The method of claim 1, wherein the optical signal is generated by exposing the captured labelled molecules to a chromogenic substrate and forming a chromogenic product.

8. The method of claim 3, wherein the labelled molecule is an enzyme or enzymatic component.

9. The method of claim 3, wherein the plurality of reaction vessels are an array of microwells.

10. The method of claim 3, wherein each reaction vessel has a defined volume between 10 attoliters and 50 picoliters.

11. The method of claim 3, wherein the ratio of molecules of target analyte to the number of reaction vessels is less than 1:1.

12. The method of claim 3, wherein the ratio of molecules of target analyte to the number of reaction vessels is less than 1:5.

13. The method of claim 3, wherein the reaction vessels are present on the surface of an array substrate.

14. The method of claim 3, wherein the step of removing any non-bound labelled molecules from the plurality of reaction vessels comprises performing a wash step.

15. The method of claim 3, further comprising sealing the reaction vessels with a sealing component such that the contents of each reaction vessel are prevented from escaping from said reaction vessel.

16. The method of claim 15, wherein molecules of the target analyte or the labelled molecules are captured prior to sealing the reaction vessels.

17. The method of claim 3, wherein the target analyte is selected from the group consisting of proteins, nucleic acids, lipids, carbohydrates, hormones, cytokines, cellular antigens, receptors, and cells.

18. The method of claim 3, wherein each reaction vessel comprises a wall that defines a binding surface that has any of the capture components that are contained in a particular reaction vessel immobilized thereon.

19. The method of claim 8, wherein the target analyte does not have enzymatic properties.

* * * * *